(12) United States Patent
Chambers

(10) Patent No.: US 10,605,789 B2
(45) Date of Patent: Mar. 31, 2020

(54) ULTRASONIC INSPECTION SYSTEM EMPLOYING SPECTRAL AND TIME DOMAIN PROCESSING OF ULTRASONIC SIGNAL

(71) Applicant: Southern Research Institute, Birmingham, AL (US)

(72) Inventor: Janelle Kay Chambers, Hoover, AL (US)

(73) Assignee: Southern Research Institute, Birmingham, AL (US)

(*) Notice: Subject to any disclaimer, the term of this patent is extended or adjusted under 35 U.S.C. 154(b) by 383 days.

(21) Appl. No.: 15/440,852

(22) Filed: Feb. 23, 2017

(65) Prior Publication Data
US 2018/0238837 A1    Aug. 23, 2018

(51) Int. Cl.
*G01N 29/34* (2006.01)
*G01N 29/04* (2006.01)
(Continued)

(52) U.S. Cl.
CPC ......... *G01N 29/348* (2013.01); *G01N 29/043* (2013.01); *G01N 29/343* (2013.01);
(Continued)

(58) Field of Classification Search
CPC .. G01N 29/348; G01N 29/043; G01N 29/343; G01N 29/42; G01N 29/46;
(Continued)

(56) References Cited

U.S. PATENT DOCUMENTS 4,949,313 A * 8/1990 Iwasawa ............. G01S 15/8959
367/7
5,303,590 A * 4/1994 Modderman ......... G01N 29/07
73/588

(Continued)

FOREIGN PATENT DOCUMENTS

WO    2016115270 A1    7/2016

OTHER PUBLICATIONS

International Search Report in corresponding PCT Application No. PCT/US2018/018994, dated May 4, 2018.

*Primary Examiner* — Nimeshkumar D Patel
*Assistant Examiner* — Nashmiya S Fayyaz
(74) *Attorney, Agent, or Firm* — Edell, Shapiro & Finnan, LLC

(57) ABSTRACT

A method performed by an ultrasonic inspection system includes delivering to a multilayer structure an ultrasonic pulse that sweeps through a chirp bandwidth, and receiving from the multilayer structure ultrasonic energy including a series of time-overlapping reflections of the pulse delivered to the multilayer structure from layers of the multilayer structure. The method also includes performing frequency domain processing on the ultrasonic energy to produce frequency resonance peaks respectively indicative of distinct layers of the multilayer structure, and performing time domain processing on the ultrasonic energy to compress the time-overlapping reflections into respective time-separated reflection time peaks. The method also includes displaying the frequency resonance peaks on a frequency domain plot, and displaying the reflection time peaks on a time domain plot.

20 Claims, 23 Drawing Sheets

(51) Int. Cl.
*G01N 29/46* (2006.01)
*G01N 29/42* (2006.01)

(52) U.S. Cl.
CPC ............. *G01N 29/42* (2013.01); *G01N 29/46* (2013.01); *G01N 2291/0231* (2013.01)

(58) Field of Classification Search
CPC ................ G01N 29/12; G01N 29/036; G01N 2291/014; G01N 2291/0231; G01H 13/00
USPC .......................................................... 73/579
See application file for complete search history.

(56) References Cited

U.S. PATENT DOCUMENTS

| | | | |
|---|---|---|---|
| 5,591,913 A * | 1/1997 | Tucker | G01N 29/12 73/602 |
| 5,637,799 A * | 6/1997 | Heyman | G01N 29/07 73/598 |
| 6,397,680 B1 * | 6/2002 | Levesque | G01B 17/025 73/579 |
| 2003/0156624 A1 * | 8/2003 | Koslar | H04B 1/69 375/131 |
| 2004/0100282 A1 | 5/2004 | Christensen et al. | |
| 2011/0144935 A1 | 6/2011 | McKeon | |
| 2012/0055253 A1 | 3/2012 | Sinha | |
| 2014/0216158 A1 * | 8/2014 | Sanabria Martin | G01N 29/069 73/588 |
| 2016/0003942 A1 * | 1/2016 | Kozuki | G01S 15/06 367/87 |
| 2016/0320346 A1 | 11/2016 | van Neer et al. | |
| 2017/0153108 A1 * | 6/2017 | Kitazawa | G01B 17/02 |
| 2018/0156756 A1 * | 6/2018 | Forster | A61J 1/035 |
| 2018/0231501 A1 * | 8/2018 | Findikoglu | G01N 29/043 |

\* cited by examiner

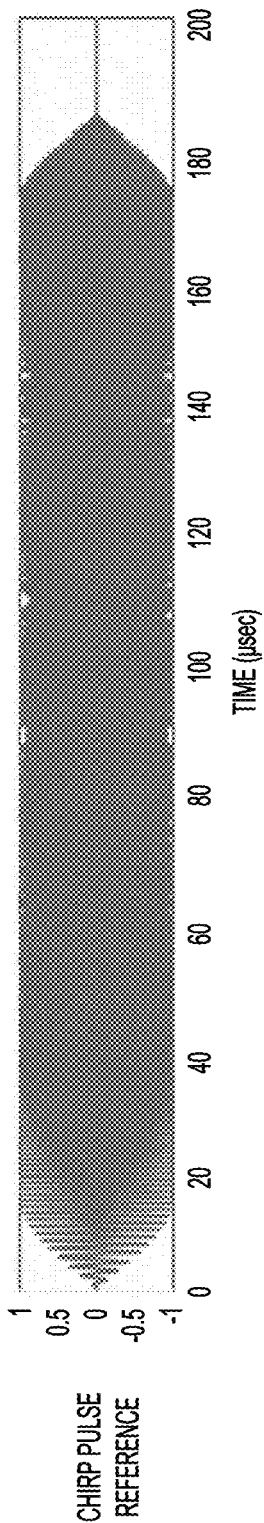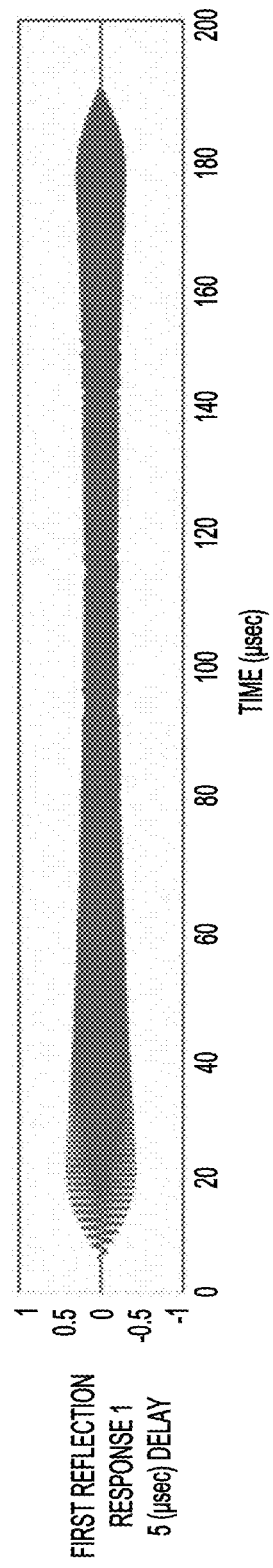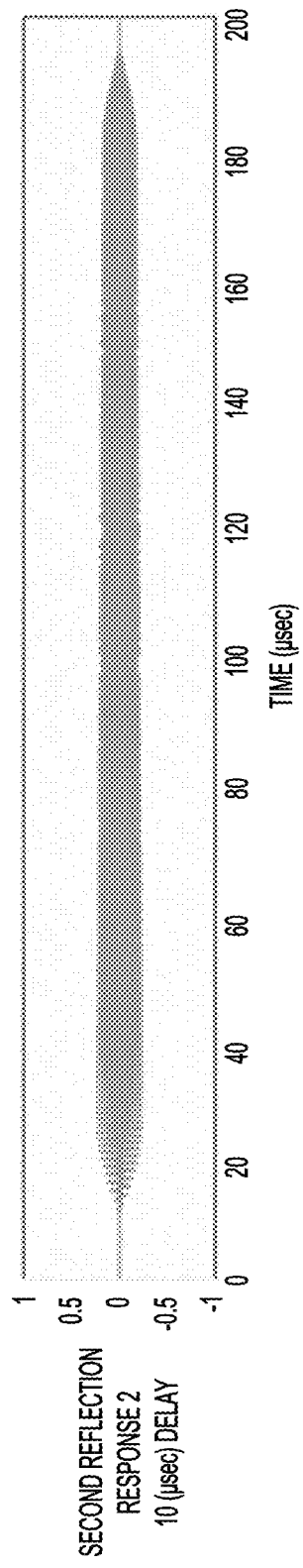

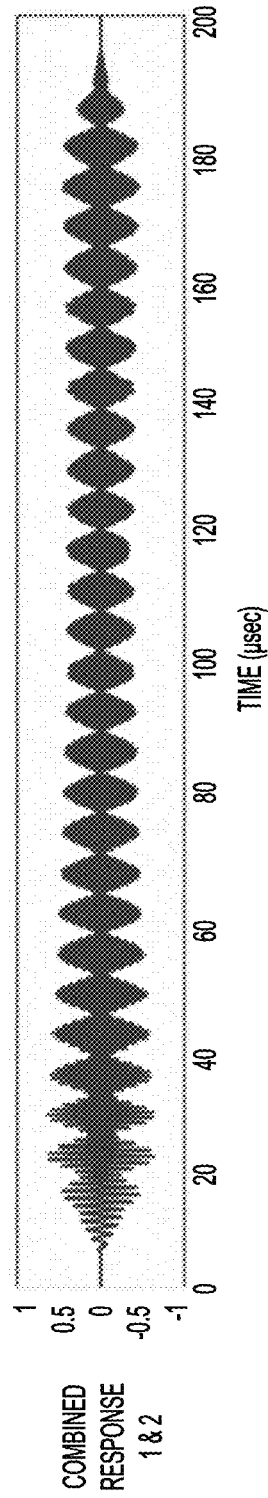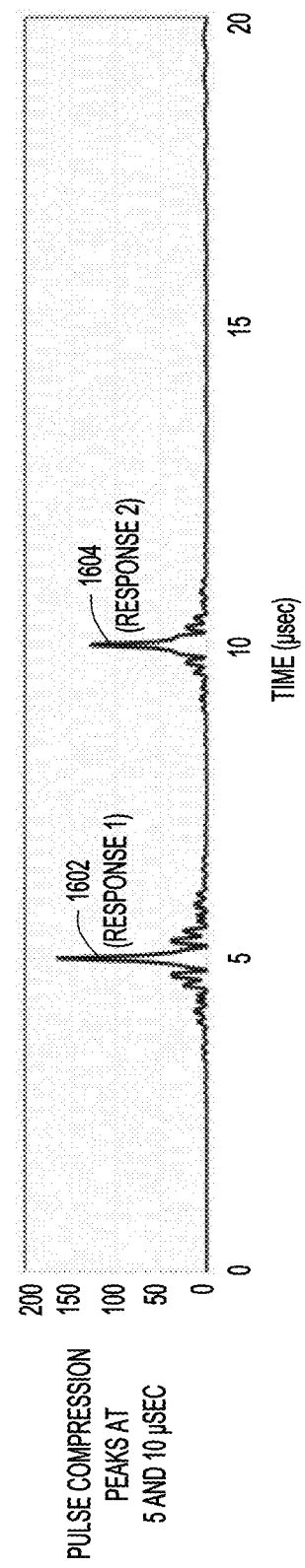

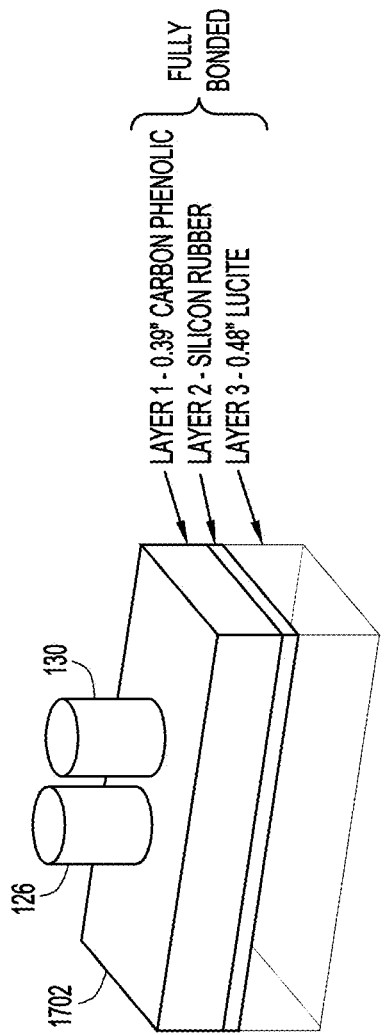
FIG. 17
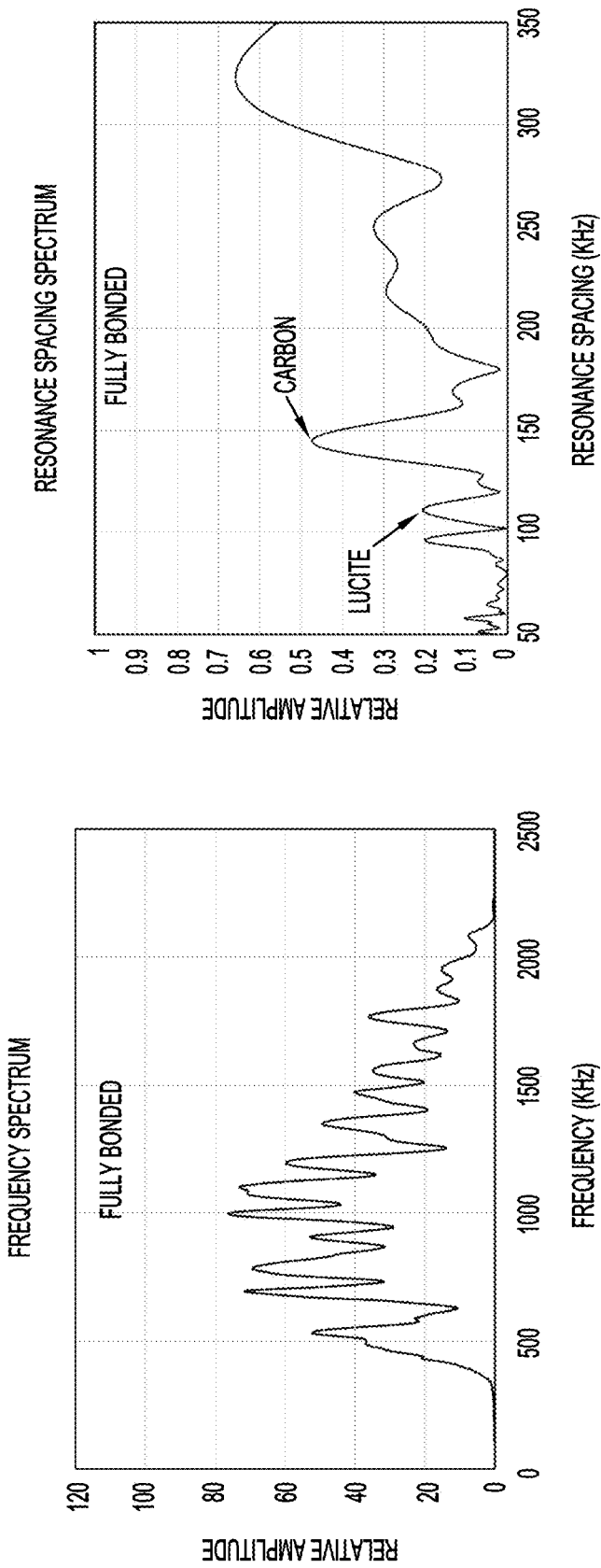
FIG. 18B
FIG. 18A

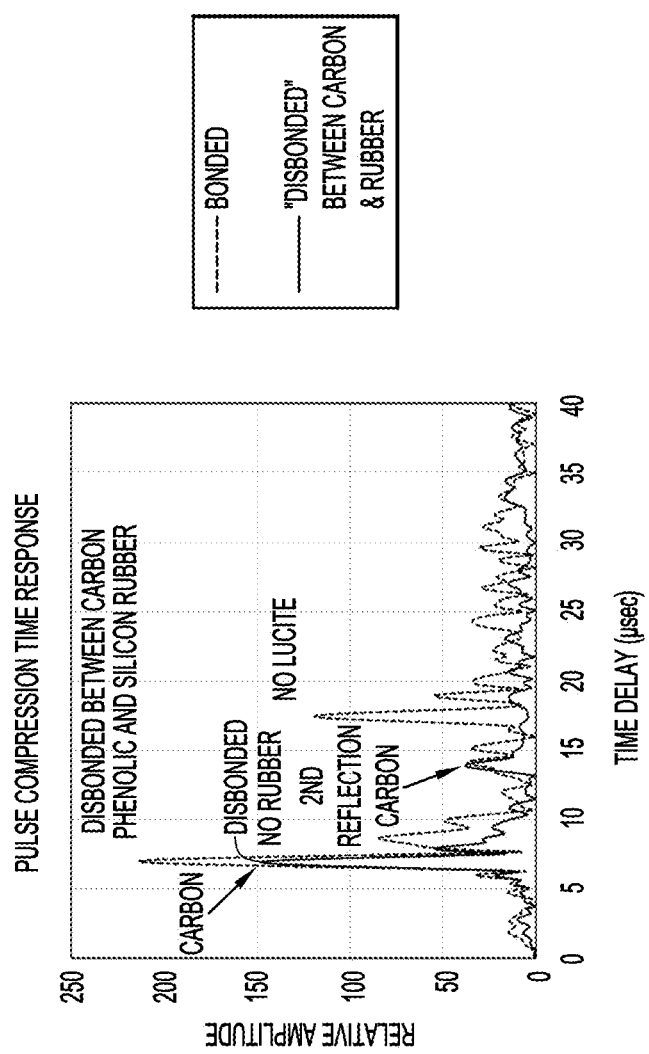

ULTRASONIC INSPECTION SYSTEM EMPLOYING SPECTRAL AND TIME DOMAIN PROCESSING OF ULTRASONIC SIGNAL

TECHNICAL FIELD

The present disclosure relates to an ultrasonic inspection system.

BACKGROUND

Ultrasonic spectroscopy uses ultrasonic energy to inspect defects and/or material properties of test materials. An ultrasonic inspection system includes ultrasonic transducers to deliver ultrasonic energy to, and detect ultrasonic energy from, the test materials. The ultrasonic inspection system analyzes the detected ultrasonic energy using ultrasonic spectroscopy techniques to expose the defects and the material properties. It is desirable to be able to deliver the ultrasonic energy to the test materials over a wide range of ultrasonic frequencies, frequency bandwidths, and amplitudes matched to a variety of properties of the test materials and operating characteristics of different transducers; however, conventional ultrasonic inspection systems operate over only a relatively narrow range of ultrasonic frequencies, frequency bandwidths, and amplitudes and suffer from both frequency and amplitude impairments outside of these narrow confines. As a result, conventional ultrasonic inspection systems limit the types of transducers that may be used and the variety of test materials that may be inspected.

Ultrasonic spectroscopy techniques may be performed on test material in the form of a single layer structure or a multilayer structure to identify/characterize composition, defects or damage in one or more layers, or bonding failures or separation between adjacent layers in a multilayer structure. One ultrasonic spectroscopy technique determines frequency responses, including material resonances in the detected ultrasonic energy. Another technique identifies time pulses in the detected ultrasonic energy. Ideally, frequency resonances are distinct from each other and the pulses are distinct from each other. In practice, however, the detected ultrasonic energy is complex because it includes time-overlapped ultrasonic energy reflections and reverberations from/caused by the different layers within the multilayer structure or a significant defect in a single layer structure. This results in destructive and constructive interference in the detected ultrasonic energy, which makes detecting distinct time reflections very difficult.

BRIEF DESCRIPTION OF THE DRAWINGS

FIG. 12 is a plot of an example chirp pulse delivered to test material by the ultrasonic transmitter.

FIG. 13 is a plot of an example first chirp pulse reflection (of the delivered chirp pulse from FIG. 12) received from the test material by the ultrasonic receiver.

FIG. 14 is a plot of an example second chirp pulse reflection (of the delivered chirp pulse from FIG. 12) received from the test material by the ultrasonic receiver.

FIG. 15 is a plot of an example combined response of the first and second chirp pulses.

FIG. 16 is a plot of example pulse compression results produced by the time domain processor based on the combined response of FIG. 15.

FIG. 17 is an illustration of another example multilayer test material.

FIG. 18A shows an example first frequency spectrum for the multilayer test material of FIG. 17 in a case where the layers of the multilayer test material are fully bonded to each other.

FIG. 18B shows an example resonance spacing spectrum for the multilayer test material of FIG. 17, based on the first frequency spectrum of FIG. 18A.

FIG. 20C is an example time domain plot of compressed pulses produced by the time domain processor corresponding to the frequency spectrums of FIGS. 20A and 20B, for the case where a second pair of layers of the multilayer test material are disbonded.

DESCRIPTION OF EXAMPLE EMBODIMENTS

Overview

A method performed by an ultrasonic inspection system includes delivering to a multilayer structure an ultrasonic pulse that sweeps through a chirp bandwidth, and receiving from the multilayer structure ultrasonic energy including a series of time-overlapping reflections of the pulse delivered to the multilayer structure from layers of the multilayer structure. The method also includes performing frequency domain processing on the ultrasonic energy to produce frequency resonance peaks respectively indicative of distinct layers of the multilayer structure, and performing time domain processing on the ultrasonic energy to compress the time-overlapping reflections into respective time-separated reflection time peaks. The method also includes displaying the frequency resonance peaks on a frequency domain plot, and displaying the reflection time peaks on a time domain plot.

Example Embodiments

Figure 1:
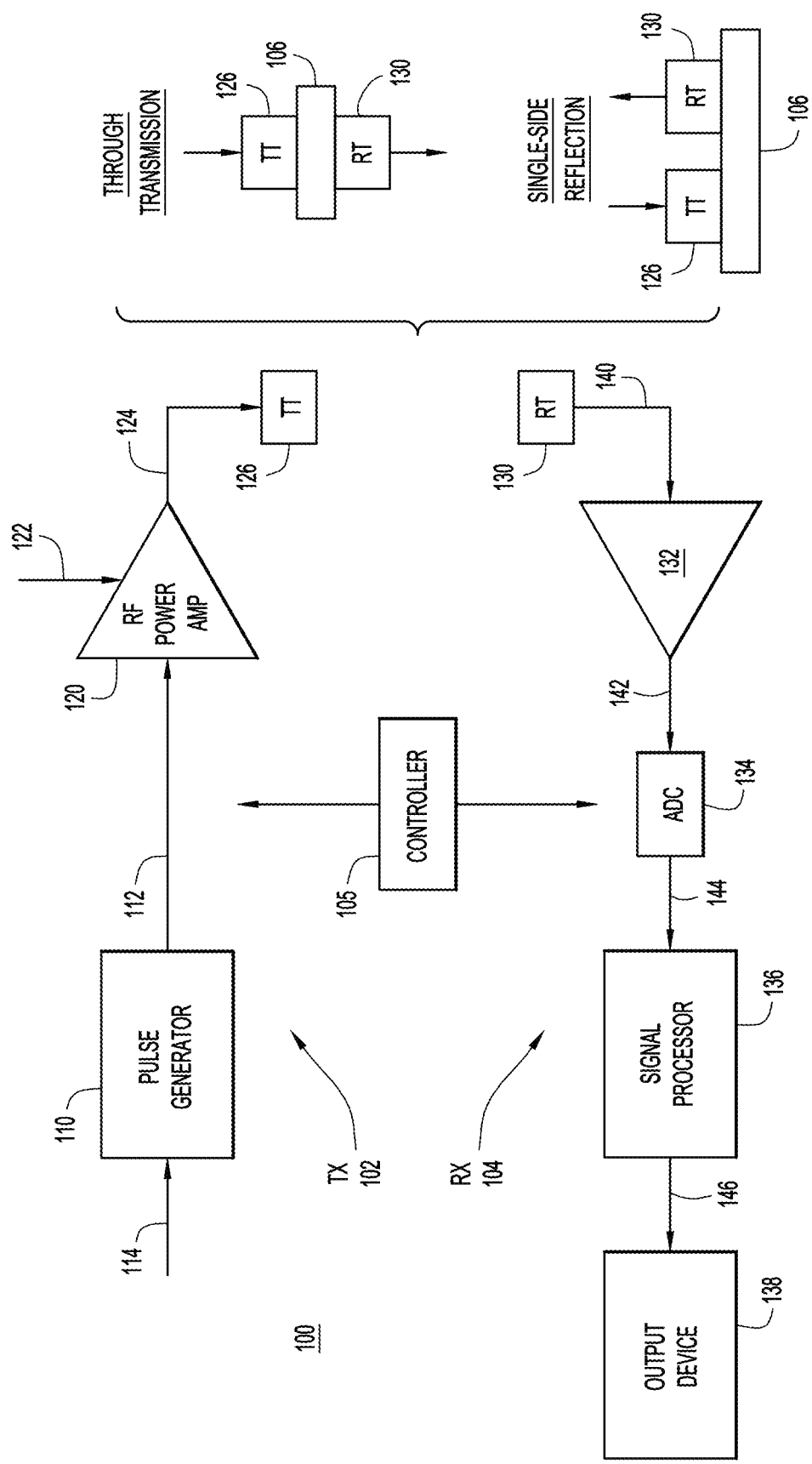
FIG. 1 is a block diagram of an example ultrasonic inspection system.

With reference to FIG. 1, there is shown a block diagram of an example ultrasonic spectroscopy inspection system 100 (referred to simply as an "ultrasonic inspection system 100") including an ultrasonic transmitter (TX) 102 and an ultrasonic receiver (RX) 104 configured to interact with each other to perform ultrasonic (spectroscopy) inspections of test material 106 coupled to both the ultrasonic transmitter and the ultrasonic receiver. In general, test material 106 can be a single layer structure, such as a monolithic piece of metal, or a multi-layer structure having two or more layers, e.g., a sandwiched structured, in which adjacent layers are designed to be bonded to each other, and where the composition may vary from layer to layer. Ultrasonic inspection system 100 may also include a controller 105, coupled to transmitter 102 and receiver 104, to provide overall control of the system and implement various functions associated with transmitter 102 and receiver 104, as described more fully below in connection with FIG. 24.

FIG. 1 shows two arrangements by which a transmit transducer 126 of transmitter 102 and a receive transducer 130 of receiver 104 are coupled to test material 106. In a "through transmission" arrangement, transmit transducer 126 is arranged on one side of test material 106 and receive transducer 130 is arranged on the opposite side of test material 106 such that receive transducer 130 receives ultrasonic transmissions that travel all the way through test material from the transmit side to the opposite receive side. This arrangement is particularly suitable where receiver 104 is designed primarily to evaluate the frequency response of test material 106 based on the received ultrasonic chirped pulse without time-domain evaluation. In the "single-sided reflection" arrangement, transmit transducer 126 and receive transducer 130 are arranged on the same side of test material 106 such that receive transducer 130 receives reflections of the ultrasonic chirped pulse instead of through transmissions. This arrangement enables the reflected ultrasonic chirped pulse to be evaluated in both the frequency domain and time domain, where individual peaks in the received time domain signal may be indicative of responses of individual layers within a multi-layer structure, the condition of inter-layer bonds, or the presence of defects within a single layer. The RF amplification scheme described herein is suitable for both the through-transmission arrangement of the transmit and receive transducers and the single-sided arrangement in which the transmit and receive transducers are located on the same side of the test material.

In either arrangement, transmitter 102 delivers an ultrasonic chirp pulse to test material 106, and receiver 104 detects resulting ultrasonic energy from the test material that is indicative of various defects and/or properties of the test material. Receiver 104 performs signal processing (referred to as ultrasonic sound analysis) on the detected ultrasonic energy to produce indications, including visual indications, of the various defects and/or properties. Depending on the transducer arrangement and the receiver capabilities, the indications may include, but are not limited to, frequency responses including material resonances, resonance spacings, and reflection time pulses, as discussed more fully below. The defects and properties indicated include, but are not limited to, a number of layers in test material 106, whether the layers are "disbonded," layer thickness, porosity, and layer composition. The term "disbonded" means there is a bonding defect between layers.

Transmitter 102 includes a pulse generator 110 to generate a chirp pulse 112 responsive to pulse generator control commands 114, a radio frequency (RF) power amplifier 120 to amplify the chirp pulse responsive to a gain control signal 122 to produce an amplified chirp pulse 124, and the ultrasonic transmit transducer (TT) 126 coupled to test material 106 so as to deliver an ultrasonic chirp pulse to the test material responsive to the amplified chirp pulse. Pulse generator 110 generates chirp pulse 112 as a sinusoidal voltage waveform, for example, that sweeps through a range of frequencies or a "swept frequency range" (also referred to as a "chirp bandwidth") from a start frequency to a stop frequency during a time period equal to a pulse width of the chirp pulse. The start frequency and the stop frequency define a frequency position of the chirp bandwidth, while a difference between the start frequency and the stop frequency defines the chirp bandwidth.

Pulse generator 110 independently adjusts chirp pulse parameters, including the start frequency, the stop frequency, the pulse width, and an amplitude of chirp pulse 112 across the chirp bandwidth, responsive to pulse generator control commands 114. Thus, the chirp bandwidth may be adjusted over a range of chirp bandwidths from a narrowest chirp bandwidth to a widest chirp bandwidth, and the frequency position of the chirp bandwidth may be adjusted over a range of frequency positions of the chirp bandwidth from a lowest frequency position to a highest frequency position. In an example, pulse generator 110 may vary (i) the chirp bandwidth from a narrow bandwidth to a broader bandwidth (e.g., up to 20 MHz), (ii) the frequency position of the chirp bandwidth (e.g., up to 40 MHz), and (iii) the amplitude from +/−0.05 volts to +/−2.0 volts. Other ranges of the chirp pulse parameters are possible. Typically, pulse generator 110 adjusts the pulse width to be approximately 40 μs or greater to ensure sufficient ultrasonic energy for inspection analysis. In operation, pulse generator 110 adjusts the aforementioned chirp pulse parameters so that they are suited to inspect defects and/or material properties of interest of test material 106.

In one embodiment, pulse generator 110 provides chirp pulse 112 to RF power amplifier 120 as a single ended voltage, in which case the RF power amplifier includes a single ended input to receive the single ended voltage. In another embodiment, pulse generator 110 provides chirp pulse 112 to RF power amplifier 120 as a differential voltage, in which case the RF power amplifier includes a differential input to receive the differential voltage. RF power amplifier 120 amplifies chirp pulse 112 received at the input of the RF power amplifier according to a gain set by gain control signal 122 to produce amplified chirp pulse 124 at an output of the RF power amplifier, and provides the amplified chirp pulse to transmit transducer 126. RF power amplifier 120 provides amplified chirp pulse 124 to a drive input of transmit transducer 126 coupled to the output of the RF power amplifier. In response to amplified chirp pulse 124, transmit transducer 126 delivers an ultrasonic chirp pulse to test material 106. Transmit transducer 126 typically represents a capacitive load to the output of RF power amplifier 120, and the capacitance of the capacitive load may vary substantially across different types of transducers. An advantage of RF power amplifier 120 is its ability to drive a wide range of capacitances (capacitive loads) over a wide range of frequencies without any appreciable degradation of power amplifier gain or effect on a frequency spectrum of amplified chirp pulse 124.

RF power amplifier 120 may be any class of RF power amplifier, e.g., Class A, Class B, Class C, and so on, configured to provide a wide operating frequency range. The wide operating frequency range represents a frequency range over which the RF power amplifier 120 provides substantial RF gain. By way of a non-limiting example, the input voltage to RF power amplifier 120 can be on the order of millivolts or tens of millivolts (e.g., 80 millivolts), while the output of RF power amplifier 120 can be on the order of tens of volts (e.g., 50 volts), with gains on the order of tens of decibels (e.g., 40 dB). The operating frequency range is wider than the widest chirp bandwidth generated by pulse generator 110. Moreover, the gain of RF power amplifier 120 is approximately flat (i.e., the gain has an approximately flat frequency response) across the widest chirp bandwidth when the widest chirp bandwidth is positioned anywhere in the operating frequency range. An example operating frequency range of RF power amplifier 120 is from 100 kHz to 40 MHz.

Figure 2:
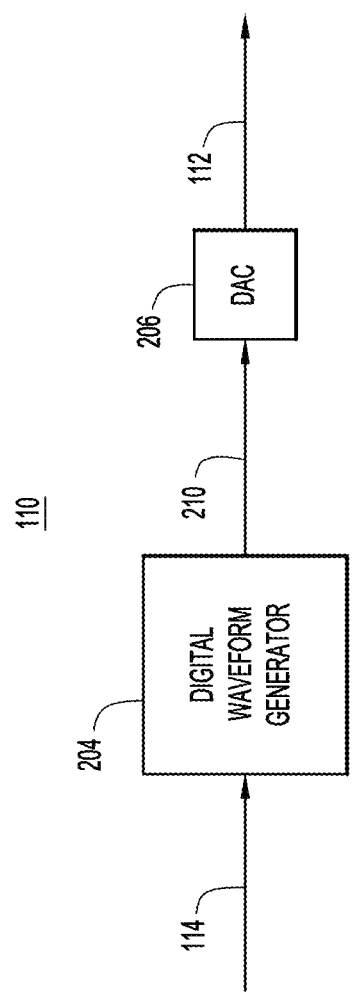
FIG. 2 is a block diagram of an example pulse generator of an ultrasonic transmitter of the ultrasonic inspection system.

With reference to FIG. 2, there is a block diagram of pulse generator 110, according to an embodiment. In the example of FIG. 2, pulse generator 110 includes a digital waveform generator 204, and a digital-to-analog converter (DAC) 206. Digital waveform generator 204 generates a digitized, frequency-swept waveform 210 responsive to pulse generator control commands 114, which also include a frequency vs. time sweep characteristic and an amplitude vs. time/frequency characteristic for the frequency-swept waveform. The frequency vs. time sweep characteristic may be in accordance with any desired frequency vs. time characteristic, e.g., the swept frequency may increase/decrease according to a linear or hyperbolic function. DAC 206 converts digitized waveform 210 to a continuous-time, chirp pulse waveform 112. Digital waveform generator 204 may be implemented based on any presently known or hereafter developed digital waveform generator techniques.

Figure 3:
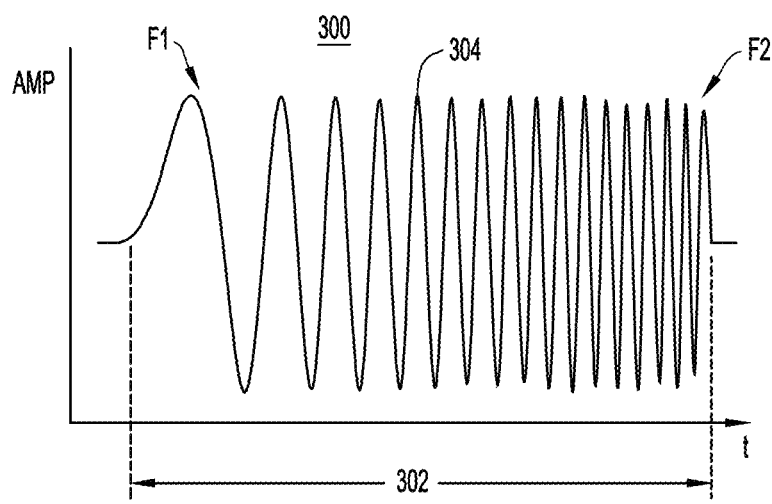
FIG. 3 is an amplitude vs. time plot of an example amplified chirp pulse produced by the ultrasonic transmitter.

With reference to FIG. 3, there is shown an amplitude vs. time plot of an idealized chirp pulse 300 delivered to test material 106 by transmit transducer 126 responsive to amplified chirp pulse 124. Chirp pulse 300 has a pulse width 302 over which a waveform 304 sweeps across a swept frequency range (i.e., chirp bandwidth) from a start frequency F1 at a start of the chirp pulse to a stop frequency F2 at an end of the chirp pulse. An amplitude of the idealized chirp pulse 300 is relatively flat or constant across the entire chirp bandwidth. In practice, to account for distortions caused by the frequency responses of transmit and receive transducers 126 and 130, a reference response waveform can be obtain by placing the transducers face to face and processing the received signal. The idealized chirp pulse 300 can than be adjusted on the transmit end (e.g., with amplitude modulation), essentially with the inverse of the distortions observed in this reference waveform, in order to compensate for the transducers' distortions. In this manner, a relatively flat frequency response can be ensured across the operating bandwidth notwithstanding the distortions introduced by the transducers.

Figure 4:
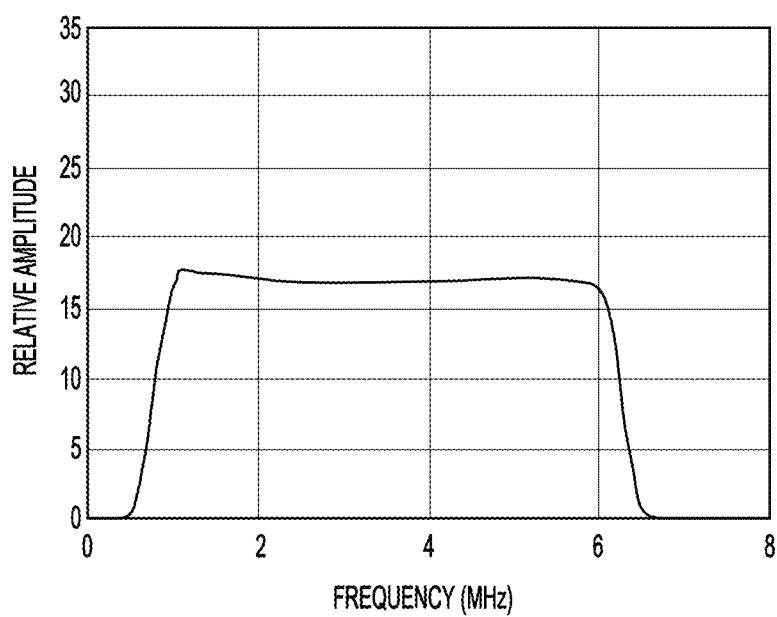
FIG. 4 shows an example frequency spectrum of the chirp pulse.

With reference to FIG. 4, there is shown an idealized frequency spectrum 400 of chirp pulse 300. Again, in order realize this frequency response at the receiver, the transmit pulse must be modified to account for the distortions from the transducers determined from a reference waveform obtained by transmitting a pulse with the transducers face to face (no intervening material). In the example of FIG. 4, start frequency F1 is approximately 1 MHz, while stop frequency F2 is approximately 6 MHz. As can be seen in FIG. 3, the chirp pulse waveform tapers into and out of the frequency sweep, resulting the bandwidth appearing slightly wider than the 1 to 6 MHz range in FIG. 4. Frequency spectrum 400 is relatively flat as a result of the above-mentioned compensation in which the reference waveform resulting from the face-to-face response of the transducers is used to offset the transducer distortions by modifying the transmit waveform.

Figure 5:
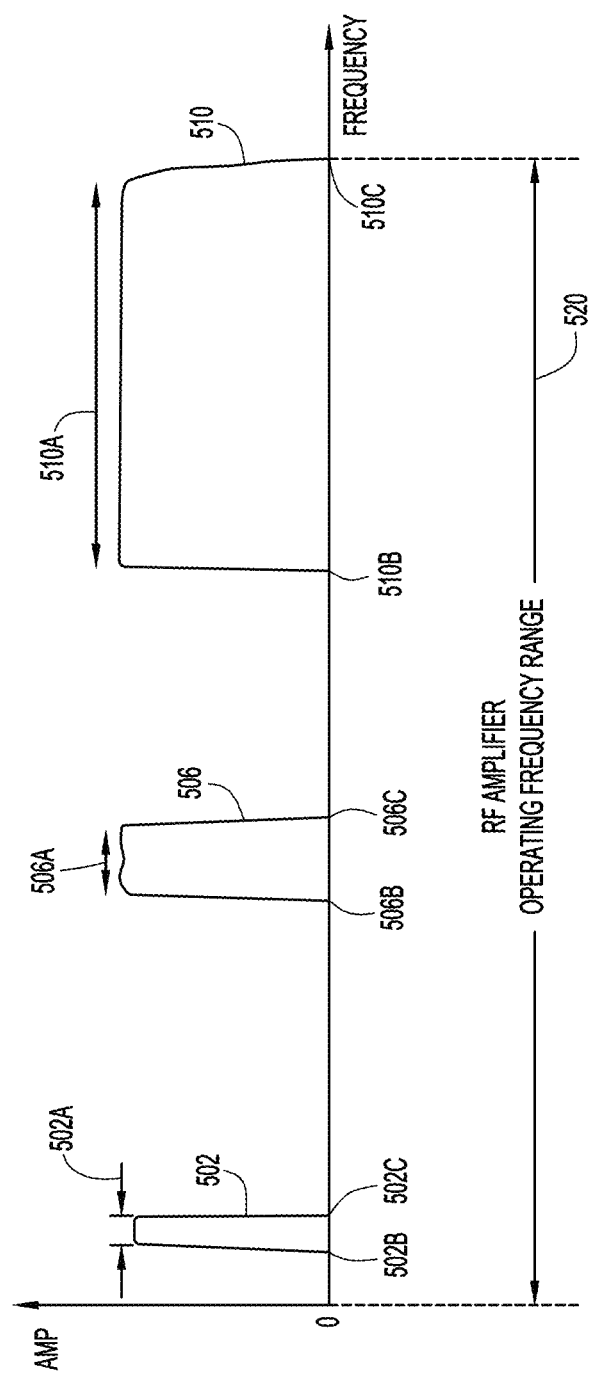
FIG. 5 shows different example frequency spectrums for different amplified chirp pulses generated by the ultrasonic transmitter.

As mentioned above, pulse generator 110 may generate chirp pulse 112 with different chirp bandwidths and frequency positions (i.e., with different pairs of start and stop frequencies) responsive to control commands 114. As an example, FIG. 5 shows different frequency spectrums for different (normalized) chirp pulses delivered by transmit transducer 126 resulting from different chirp pulses (112) generated by signal generator 110. The frequency spectrums include a first frequency spectrum 502 having a first chirp bandwidth 502A (e.g., 450 kHz) positioned at first start and stop frequencies 502B, 502C (e.g., 50 kHz, 500 kHz), a second frequency spectrum 506 having a second chirp bandwidth 506A (e.g., 6 MHz) positioned at second start and stop frequencies 506B, 506C (e.g., 1 MHz, 7 MHz), and a third frequency spectrum 510 having a third chirp bandwidth 510A (e.g., 20 MHz) positioned at third start and stop frequencies 510B, 510C (e.g., 20 MHz, 40 MHz). Frequency spectrums 502-510 all fall within wide operating bandwidth 520 of RF power amplifier 120 and, therefore, benefit from the relatively high, relatively flat gain of the RF power amplifier across each of chirp bandwidths 502A, 506A, and 510A.

Pulse generator 110 controls an amplitude, e.g., peak-to-peak voltage, of chirp pulse 112 to avoid over driving RF power amplifier 120. When RF power amplifier 120 is over driven, the RF power amplifier clips the amplitude (e.g., sinewave clipping) of amplified chirp pulse 124. Therefore, pulse generator 110 generates chirp pulse 112 so that its amplitude remains just below an amplitude (referred to as a "limit amplitude") that over drives RF power amplifier 120. Typically, the limit amplitude is frequency dependent, e.g., increases with frequency, across the operating frequency range of RF power amplifier 120. Thus, pulse generator 110 may control the amplitude of chirp pulse 112 to track the limit amplitude over frequency, e.g., to increase the amplitude of chirp pulse 112 with frequency in correspondence with an increase in the limit amplitude with frequency. The limit amplitude variations across the operating frequency range of RF power amplifier 120 may be determined empirically, and the amplitude of chirp pulse 112 may be adjusted to be just below the empirically determined limit amplitude based on control commands 114. In an example, the peak-to-peak voltage of chirp pulse 112 may be controlled to be in a range from +/−0.05 volts to +/−1.0 volts from a low end of the operating frequency range to a high end of the operating frequency range, to produce a relatively constant peak-to-peak voltage of amplified chirp pulse 124 of approximately +/−80 volts.

Additionally, as previously described, pulse generator 110 controls the amplitude of chirp pulse 112 to modify the amplitude of the ultrasonic energy delivered by transmit transducer 126 to test material 106 over the chirp bandwidth in order to compensate for transducer distortions determined from the reference waveform. While it is preferable to deliver a chirp pulse having a flat frequency spectrum to test material 106, a combined frequency response of RF power amplifier 120, transmit transducer 126, and receive transducer 130 may vary across a given chirp bandwidth. Accordingly, pulse generator 110 varies the amplitude of chirp pulse 112 across the chirp bandwidth to compensate for/cancel the way in which the combined frequency response varies across the chirp bandwidth, so that transducer 126 delivers the chirp pulse to test material 106 with a compensated or "normalized," flat frequency spectrum. For example, pulse generator 110 increases or decreases the amplitude of chirp pulse 112 over the chirp bandwidth in a manner that essentially applies the inverse of the frequency distortions observed in the reference waveform at the receiver as a result of a test transmission with the transmit and receive transducer placed face to face with no intervening test material. This compensation provides a normalized/flat frequency spectrum (of the chirp pulse) at the receiver. Essentially, the use of the reference waveform enables the combined frequency response of RF power amplifier 120, transmit transducer 126, and receive transducer 130 over the chirp bandwidth may be characterized/measured. During regular operation, when pulse generator 110 generates chirp pulse 112 to inspect test material 106, the pulse generator controls (increases/decreases) the amplitude of chirp pulse 112 over the chirp bandwidth based on (i.e. to compensate for) the characterized/measured combined frequency response.

Referring again to FIG. 1, receiver 104 is now described with particular emphasis on the combination of both frequency domain and time domain process. It will be appreciated, however, that the above-described transmitter 102 and amplification scheme is suitable for operation in ultrasonic systems that do not employ all of the aspects of the described receiver 104. Receiver 104 includes an ultrasonic receive transducer 130 coupled to test material 106, a receive amplifier 132, an analog-to-digital converter (ADC) 134, a signal processor 136 (also referred to as an "ultrasonic sound analyzer 136"), and an output device 138, such as a computer display. When transmit transducer 126 delivers an ultrasonic chirp pulse to test material 106, receive transducer 130 detects from the test material an ultrasonic signal 140 (also referred to as ultrasonic energy 140) resulting from an interaction between the delivered ultrasonic chirp pulse and the test material, and provides the detected ultrasonic signal to receive amplifier 132.

Receive amplifier 132 amplifies ultrasonic signal 140 to produce an amplified ultrasonic signal 142, and provides the amplified ultrasonic signal to ADC 134. ADC 134 digitizes amplified ultrasonic signal 142 to produce a digitized ultrasonic signal 144 (representative of ultrasonic signal 140), and provides the digitized ultrasonic signal to signal processor 136. Signal processor 136 processes digitized ultrasonic signal 144 (also referred to as digitized ultrasonic energy 144) to produce processing results 146, stores the processing results, and provides the processing results to output device 138, e.g., for display. Processing results 146 provide visual indications or representations of defects and the various properties of interest of test material 106.

Figure 6:
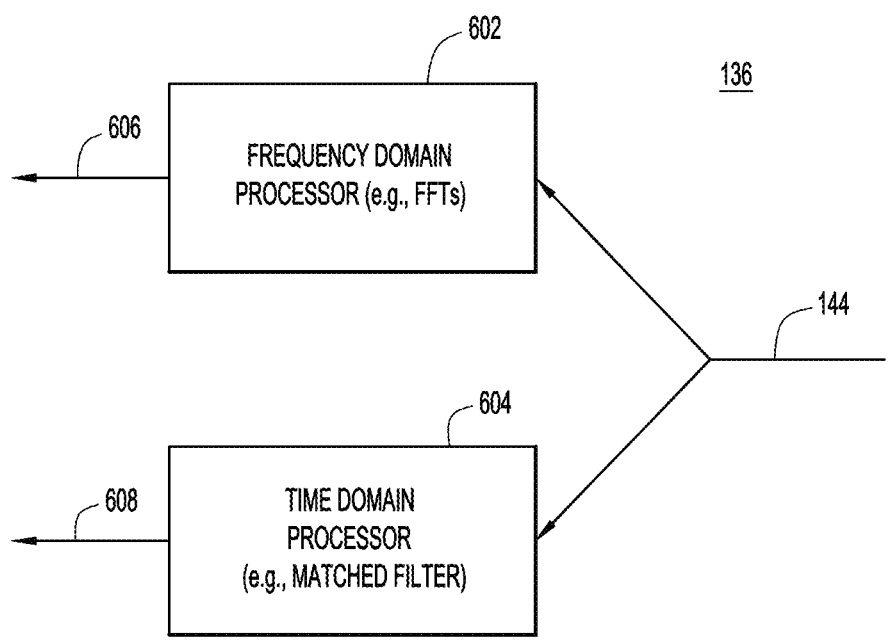
FIG. 6 is a block diagram of an example signal processor of an ultrasonic receiver of the ultrasonic inspection system.

With reference to FIG. 6, there is a block diagram of signal processor 136, according to an embodiment. Signal processor 136 includes a frequency domain/spectral processor 602 to perform frequency domain or spectral processing on digitized ultrasonic signal 144, to produce spectral processing results 606 (included in results 146) for display. Signal processor 136 also includes a time domain processor 604 to perform time domain processing on digitized ultrasonic signal 144, to produce time domain processing results 608 (also included in results 146) for display. Frequency domain processor 602 and time domain processor 604 process digitized ultrasonic signal 144 in parallel and are thus able to (i) perform their respective spectral and time domain processing on the same ultrasonic signal, concurrently, and (ii) deliver their respective results 606, 608 to output device 138, concurrently. In other embodiments, processors 602 and 604 may perform their respective processing sequentially.

Spectral processor 602 performs Fourier transforms, e.g., Fast Fourier transforms (FFTs), on digitized ultrasonic signal 144 to generate frequency spectrums of the ultrasonic signal. The frequency spectrums show frequency resonances produced by the interaction of the chirp pulse delivered to test material 106 and one or more layers of the test material. The frequency resonances indicate various properties of the one or more layers. In an embodiment, spectral processor 602 performs (i) a first FFT on digitized ultrasonic signal 144 to produce a first frequency spectrum, and (ii) a second FFT on the first frequency spectrum to produce a second frequency spectrum, referred to as a "resonance spacing spectrum." The second spectrum shows frequency spacings between frequency resonances of the first frequency spectrum, hence the name "resonance spacing spectrum." Both the first and second frequency spectrums may be included in spectral processing results 606, and displayed on output device 138.

Figure 7B:
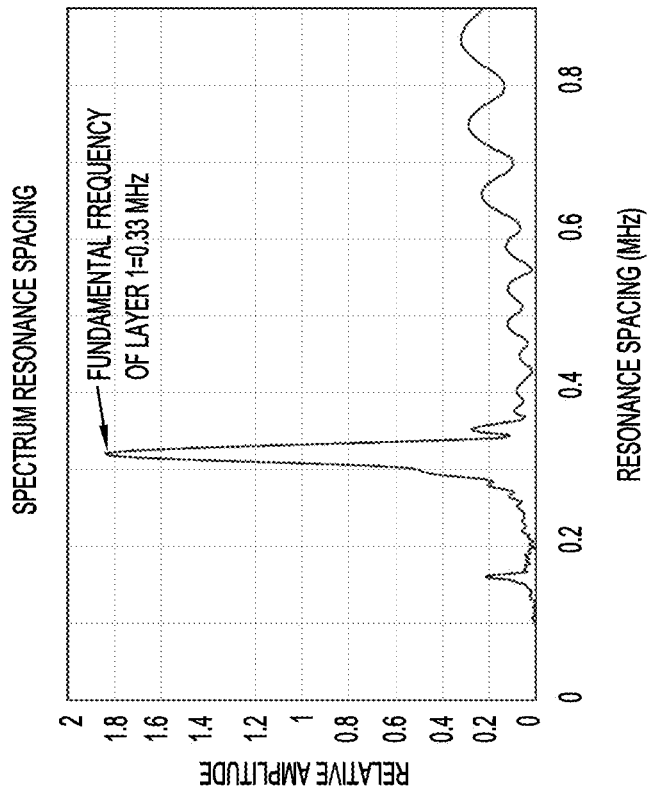
FIG. 7B shows an example second frequency spectrum (i.e., resonance spacing spectrum) produced by the spectral processor for the single graphite epoxy layer based on the first frequency spectrum.
Figure 7A:
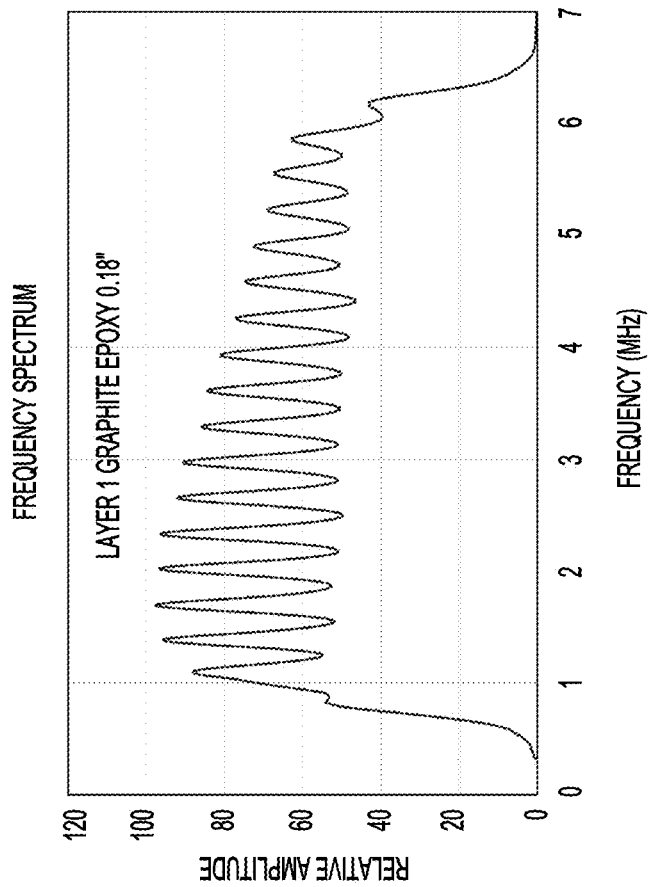
FIG. 7A shows an example first frequency spectrum produced by a frequency domain/spectral processor of the signal processor for a single graphite epoxy layer.

With reference to FIG. 7A, there is shown an example first frequency spectrum produced by spectral processor 602 (as described above) when transmitter 102 delivers an ultrasonic chirp pulse to a single graphite epoxy layer, 0.18" thick, coupled to transmit and receive transducers 126 and 130. The chirp pulse has a chirp bandwidth of 6 MHz and is positioned in frequency at 0.5 MHz to 6.5 MHz. The first frequency spectrum prominently shows multiple frequency harmonics of a fundamental (resonance) frequency indicative of the graphite epoxy layer.

With reference to FIG. 7B, there is shown an example second frequency spectrum produced by spectral processor 602, as an FFT of the first frequency spectrum from FIG. 7A. The second frequency spectrum prominently shows the fundamental (resonance) frequency of 0.33 MHz for the graphite epoxy layer (referred to as "Layer 1").

Figure 8B:
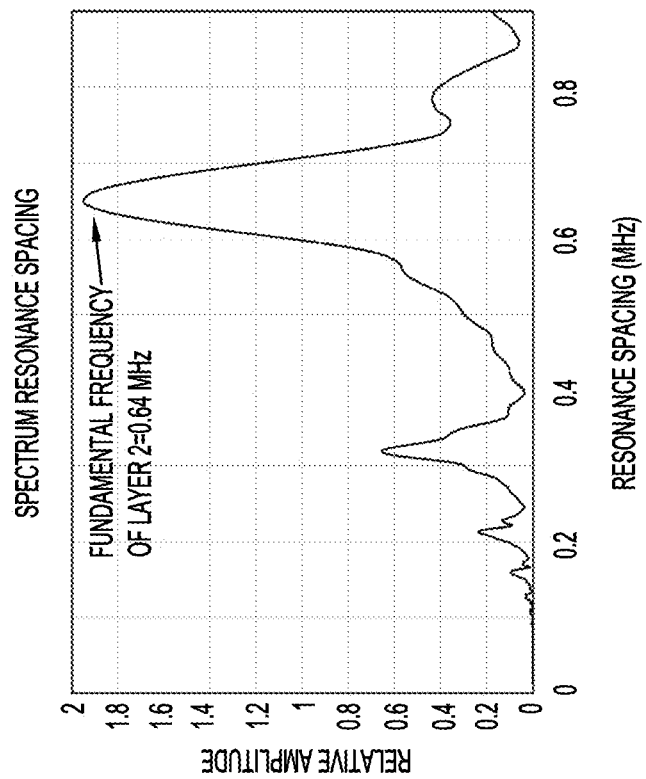
FIG. 8B shows an example resonance spacing spectrum for the single silicon rubber layer, based on the first frequency spectrum of FIG. 8A.
Figure 8A:
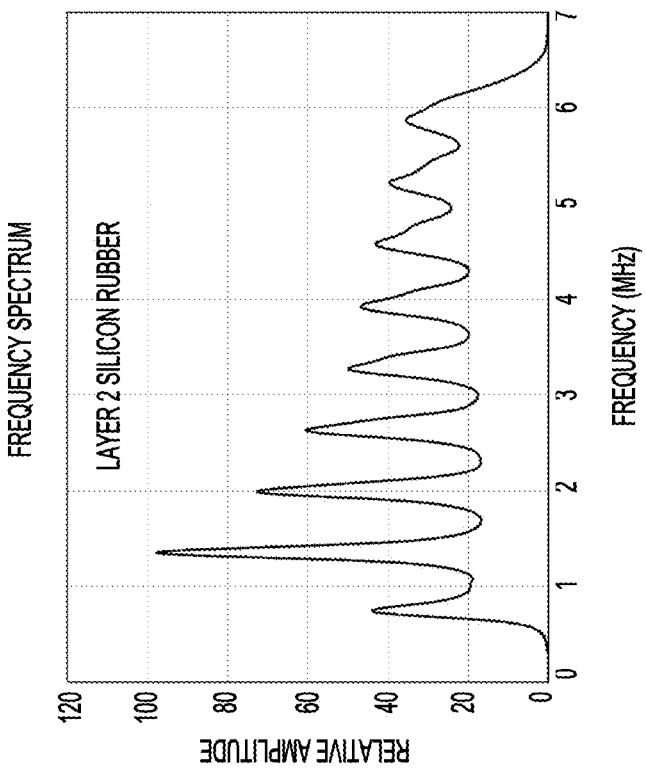
FIG. 8A shows an example first frequency spectrum for a single silicon rubber layer.

With reference to FIG. 8A, there is shown an example first frequency spectrum produced by spectral processor 602 when transmitter 102 delivers the same chirp pulse used in connection with FIGS. 7A and 7B to a single silicon rubber layer, which may be used as an adhesive or bonding layer between other layers. The first frequency spectrum prominently shows multiple frequency harmonics of a fundamental (resonance) frequency indicative of the silicon rubber layer.

With reference to FIG. 8B, there is shown an example second frequency spectrum produced by spectral processor 602, as an FFT of the first frequency spectrum from FIG. 8B. The second frequency spectrum prominently shows the fundamental (resonance) frequency of 0.64 MHz for the silicon rubber layer (referred to as "Layer 2").

Figure 9B:
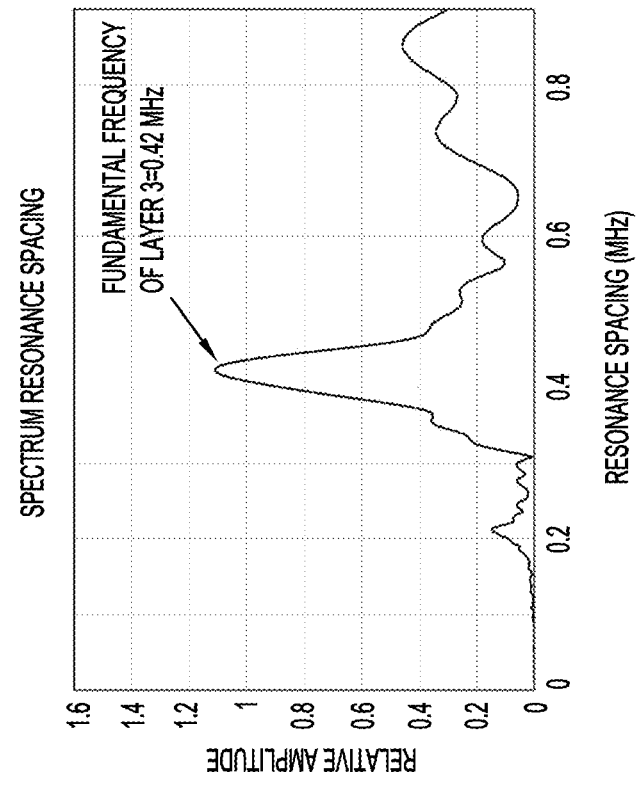
FIG. 9B shows an example resonance spacing spectrum for the single graphite epoxy layer of different thickness, based on the first frequency spectrum of FIG. 9A.
Figure 9A:
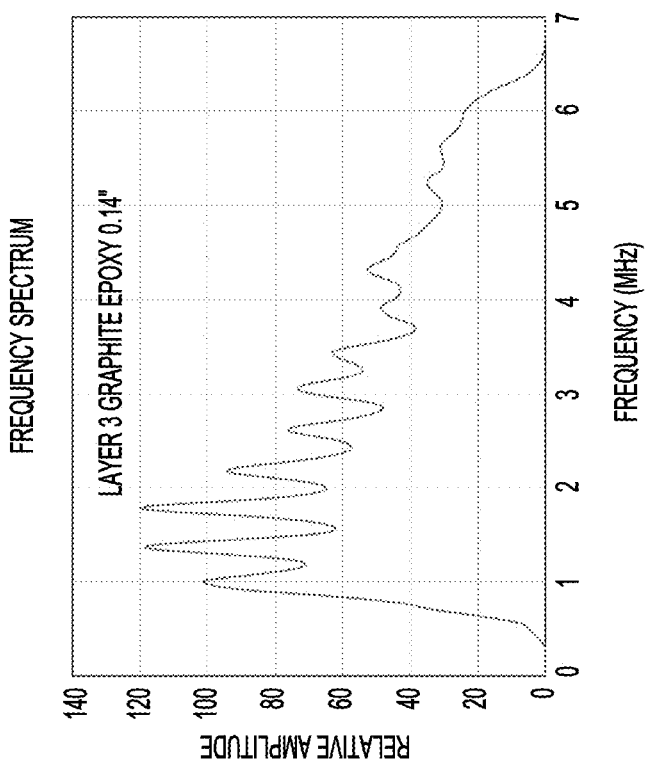
FIG. 9A shows an example first frequency spectrum for a single graphite epoxy layer of different thickness than the layer for FIG. 7A.

With reference to FIG. 9A, there is shown an example first frequency spectrum produced by spectral processor 602 when transmitter 102 delivers the same chirp pulse used in connection with FIGS. 7A and 8A to a single graphite epoxy layer 0.14" thick. The first frequency spectrum prominently shows multiple frequency harmonics of a fundamental (resonance) frequency indicative of the graphite epoxy layer.

With reference to FIG. 9B, there is shown an example second frequency spectrum produced by spectral processor 602, as an FFT of the first frequency spectrum from FIG. 9B. The second frequency spectrum prominently shows the fundamental (resonance) frequency of 0.42 MHz for the graphite epoxy layer (referred to as "Layer 3").

Figure 10A:
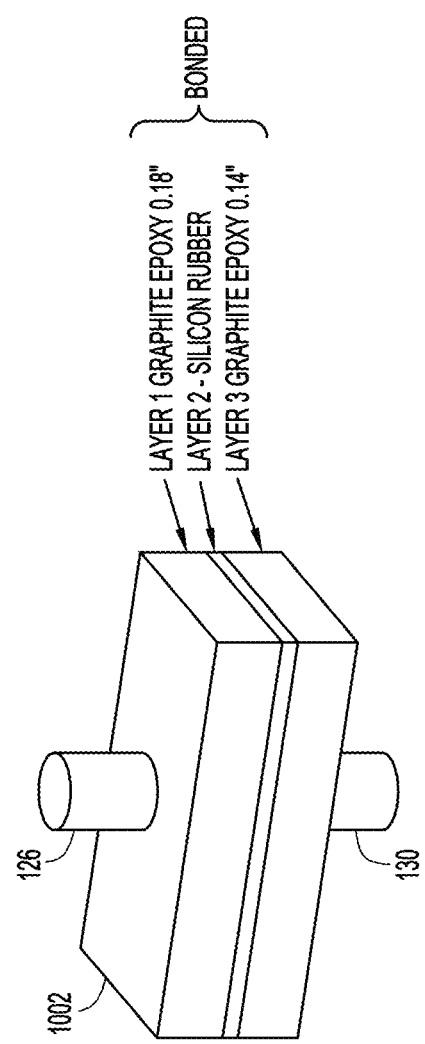
FIG. 10A is an illustration of example multilayer test material in which the single layers examined in FIGS. 7A, 8A, and 9A are bonded together.

With reference to FIG. 10A, there is an illustration of test material 1002 having transmit transducer 126 coupled to an upper face of the test material and receive transducer 130 coupled to a bottom face of the test material that opposes the upper face. Test material 1002 is a multilayer structure that includes a Layer 1 (a graphite epoxy layer 0.18" thick), a Layer 2 (a silicon rubber layer), and a Layer 3 (a graphite epoxy layer 0.14" thick) bonded together via the silicon rubber layer. The layers Layer 1, Layer 2, and Layer 3 are the same as those discussed above in connection with FIGS. 7A, 7B), (8A, 8B), and (9A, 9B), respectively.

Figure 10C:
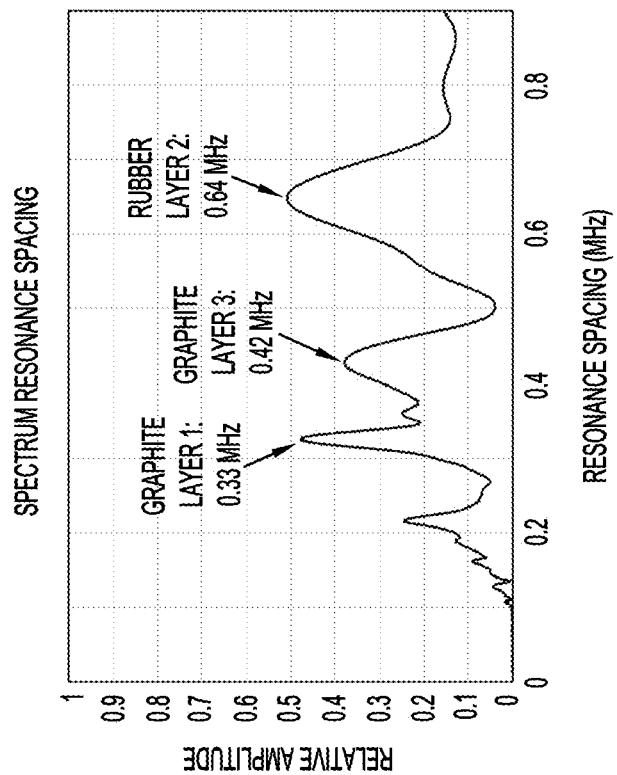
FIG. 10C shows an example resonance spacing spectrum for the multilayer test material, based on the first frequency spectrum of FIG. 10B.
Figure 10B:
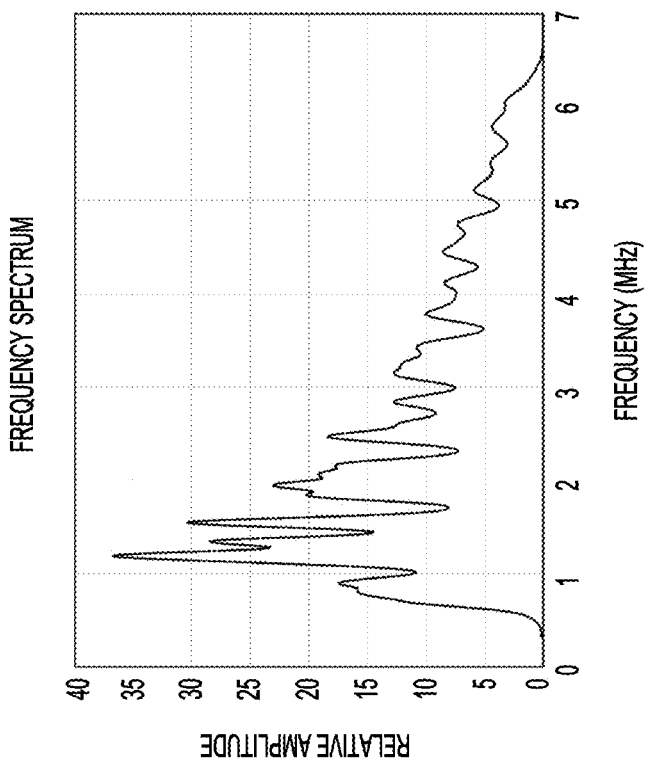
FIG. 10B shows an example first frequency spectrum for the multilayer test material.

With reference to FIG. 10B, there is shown an example first frequency spectrum produced by spectral processor 602 when transmitter 102 delivers the chirp pulse used in connection with FIGS. 7A, 8A, and 9A to test material 1002. The first frequency spectrum shows a combination of frequency harmonics indicative of each of the 3 layers.

With reference to FIG. 10C there is shown an example second frequency spectrum produced by spectral processor 602, as an FFT of the first frequency spectrum of FIG. 10B. The second frequency spectrum prominently shows fundamental frequencies for all three layers and from which the 3 layers can be identified.

As mentioned above, time domain processor 604 performs time domain processing on digitized ultrasonic signal 144 (which is representative of ultrasonic signal 140). Ultrasonic signal 140/144 includes reflections of the chirp pulse delivered to test material 106 from one or more layers of the test material. The reflections may be referred to as "reflected chirp pulses" or "chirp pulse reflections." Because the layers are relatively thin, the chirp pulse reflections have reflection times between layers (e.g., 5 or 10 µs) that are much shorter than their pulse widths (e.g., 200 µs). This causes substantial time-overlapping of the chirp pulse reflections. Overlapping chirp pulse reflections tend to constructively and destructively interfere with each other. Consequently, ultrasonic signal 140/144 includes a series of time-overlapping (and interfering) chirp pulse reflections. The time-overlapping chirp pulse reflections subside over a finite time. The finite time during which the time-overlapping chirp pulse reflections persist is referred to as a "full multilayer response" of the test material 106. The full multilayer response is analogous to an impulse response of a system driven by an impulse, where the impulse is the chirp pulse delivered to test material 106 (representing the system).

Time domain processor 604 performs time domain processing on the series of time-overlapping chirp pulse reflections of the full multilayer response to compress each of the reflections into a respective compressed pulse (also referred to as a "reflection time peak"), such that the resulting compressed pulses are spaced apart from each other in time, i.e., they are not time-overlapping. In this way, the time-separated compressed pulses each indicate a distinct reflection or layer interface in test material 106. In an embodiment, time domain processor 604 includes a matched filter to filter the series of time-overlapping chirp pulse reflections included in ultrasonic signal 140/144. The matched filter is matched to the swept frequency characteristic of the chirp pulse, i.e., the time vs. frequency characteristic of the swept waveform generated by pulse generator 110.

Figure 11:
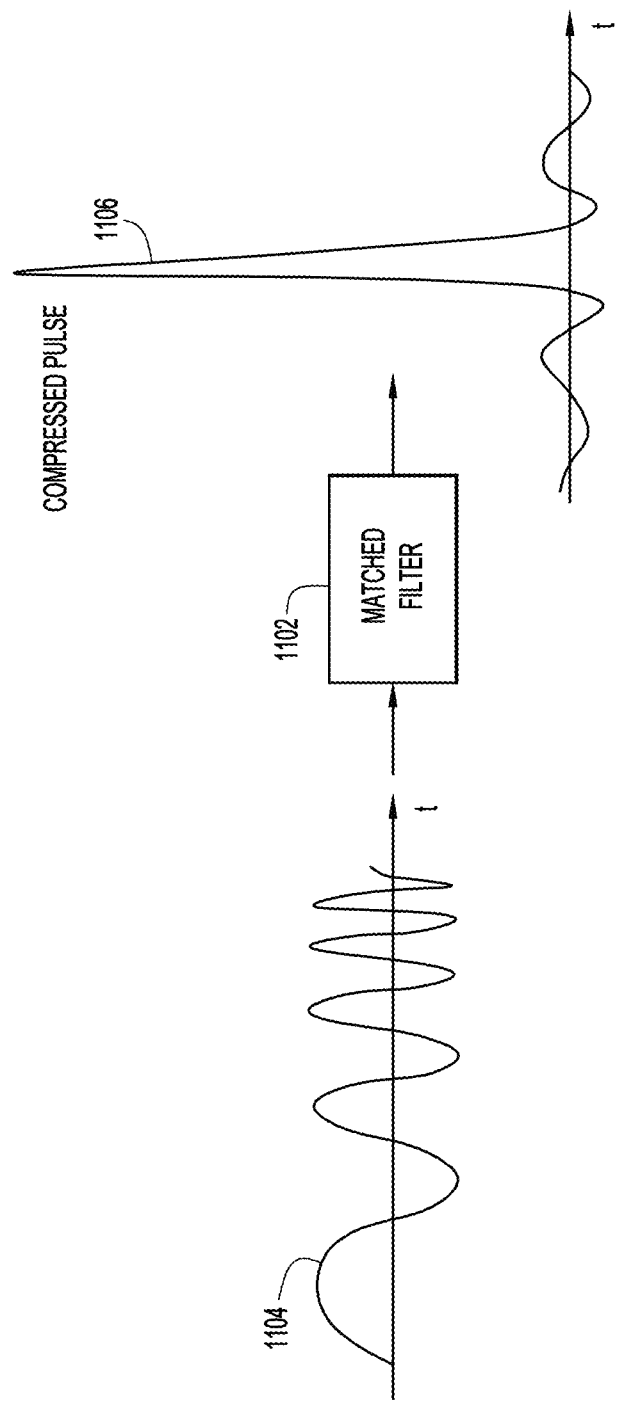
FIG. 11 is an illustration of an example matched filter in a time domain processor of the signal processor.

With reference to FIG. 11, there is an illustration of a matched filter 1102 included in time domain processor 602. Matched filter 1102 receives a chirp pulse 1104 in ultrasonic signal 140/144 (e.g., which may be a reflection of the chirp pulse delivered to test material 106 from one of the layers of the test material). Matched filter 1102 filters/compresses chirp pulse 1104 (e.g., the reflection) to produce compressed pulse 1106 (e.g., as a "reflection time peak"), which has a pulse width that is substantially shorter than that of the received chirp pulse. The operations performed by time domain processor 602 and its outputs are described further in connection with FIGS. 12-16.

With reference to FIG. 12, there is a plot of an example chirp pulse delivered by transmitter 102 to test material 106 at a start time of 0 microseconds (µs). The chirp pulse has a pulse width of approximately 185 µs.

With reference to FIG. 13, there is a plot of a first reflection of the delivered chirp pulse (i.e., a first chirp pulse reflection, referred to as "Response 1") received by receiver 102 from test material 106, a time delay of 5 µs. The first chirp pulse reflection may be a reflection of the delivered chirp pulse from a first layer of test material 106.

With reference to FIG. 14, there is a plot of a second reflection of the delivered chirp pulse (i.e., a second chirp pulse reflection, referred to as "Response 2") received by receiver 102 from test material 106, after a time delay of 10 µs. The second chirp pulse reflection may be a reflection of the delivered chirp pulse from a second layer of test material 106. The first and second chirp pulse reflections are time-overlapped over most of their respective pulse widths and together form a combined response, shown in FIG. 15.

With reference to FIG. 15, there is a plot of the combined response (referred to as "combined response 1 & 2") received from test material 106. The combined response exhibits both constructive and destructive interference between Response 1 and Response 2.

Time domain processor 602 performs pulse compression on the combined response to produce pulse compression results, as shown in FIG. 16. FIG. 16 is a time domain plot of the pulse compression results, which include (i) a first compressed pulse 1602 (i.e., a first reflection time peak 1602) representative of the first chirp pulse reflection Response 1, and (ii) a second compressed pulse 1604 (i.e., a second reflection time peak 1604) representative of the second chirp pulse reflection Response 2. Unlike the respective reflections from which they were derived, compressed pulses 1602 and 1604 are distinct because they are non-overlapped in time, i.e., are spaced-apart from each other. Accordingly, distinct compressed pulses 1602, 1604 clearly indicate respective distinct layers of test material 106.

With reference to FIG. 17, there is an illustration of multilayered test material 1702 having transmit transducer 126 and receive transducer 130 coupled to the same (upper) face of the test material. Multilayer test material 1702 includes a carbon phenolic layer (Layer 1) 0.39" thick, a silicon rubber layer (Layer 2), and a Lucite layer (Layer 3) 0.48" thick bonded together. With the arrangement shown in FIG. 17, transmitter 102 delivers a chirp pulse to multilayer test material 1702. The delivered chirp pulse has a pulse width of approximately 185 μs, a chirp bandwidth of approximately 1900 kHz, and is positioned in frequency at approximately 300 kHz to 2200 kHz.

Figure 18C:
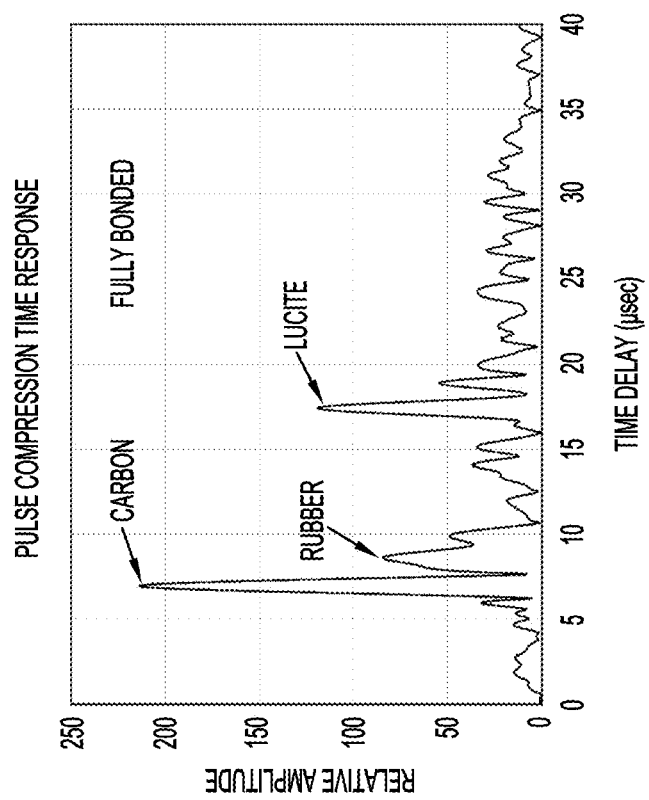
FIG. 18C is an example time domain plot of compressed pulses produced by the time domain processor corresponding to the frequency spectrums of FIGS. 18A and 18B, for the fully bonded multilayer test material.

FIGS. 18A-18C show inspection results for test material 1702 produced by receiver 104 responsive to the delivered chirp pulse as described in connection with FIG. 17.

With reference to FIG. 18A there is shown an example first frequency spectrum produced by spectral processor 602 (as described above).

With reference to FIG. 18B there is shown an example second frequency spectrum produced by spectral processor 602, as an FFT of the first frequency spectrum from FIG. 18A. The second frequency spectrum prominently shows the resonance frequencies for the Lucite layer (Layer 3) and the carbon phenolic layer (Layer 1), but not the silicon rubber layer (Layer 2). The resonance frequency is too high to have multiple peaks in this frequency range.

With reference to FIG. 18C, there is shown an example time domain plot produced by time domain processor 604. The time domain plot includes a compressed pulse corresponding to a reflection from the carbon phenolic layer (Layer 1), a compressed pulse corresponding to a reflection from the silicon rubber layer (Layer 2), and a compressed pulse corresponding to a reflection from the Lucite layer (Layer 3). The aforementioned compressed pulses are non-overlapping in time. Thus, each compressed pulse is indicative of a corresponding one of the layers, Layer 1-3. While the resonance for the silicon rubber layer Layer 2 is missing from the second frequency spectrum of FIG. 18B, that layer is clearly indicated by a compressed pulse on the time domain plot of FIG. 18C. Thus, an advantage of performing both spectral processing and time domain processing (to perform pulse compression of the reflected chirp pulses) concurrently on the same received ultrasonic signal, and then displaying the respective processing results concurrently on one or more displays, is that the combination of techniques provides a more complete picture of the defects and/or properties of the test material. For example, when the frequency domain processing on the ultrasonic energy causes respective frequency resonance peaks corresponding to distinct layers of the multilayer structure having a same frequency resonance to overlap in a combined frequency resonance peak such that the distinct layers are not separately indicated on the frequency domain plot, but the time domain processing results in time-separated reflection time pulses that separately indicate the distinct layers on the time domain plot, then displaying results of both the frequency domain processing and the time domain processing allows comparison between the two for a more complete picture of the test material.

Figures 19A, 19B:
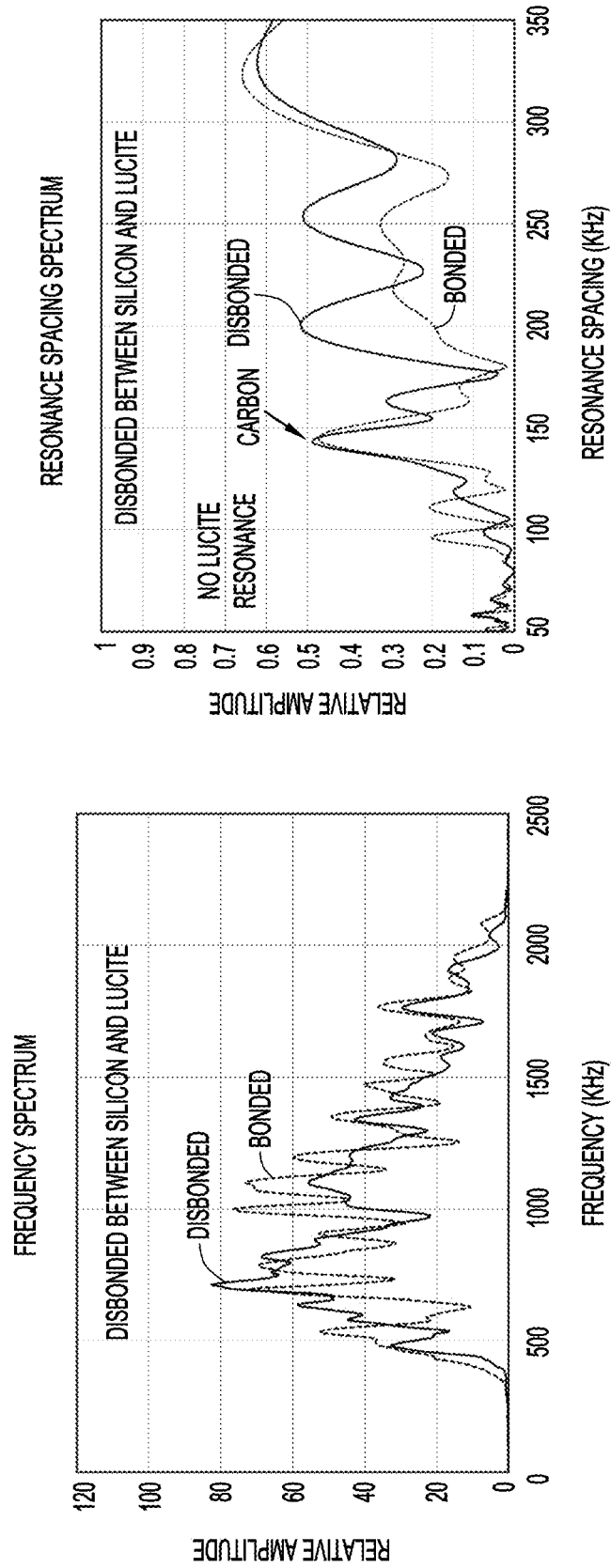
FIG. 19A shows an example first frequency spectrum for the multilayer test material of FIG. 17 in a case where a first pair of the layers of the multilayer test material are disbonded.
FIG. 19B shows an example resonance spacing spectrum for the multilayer test material of FIG. 17, based on the first frequency spectrum of FIG. 19A.
Figure 19C:
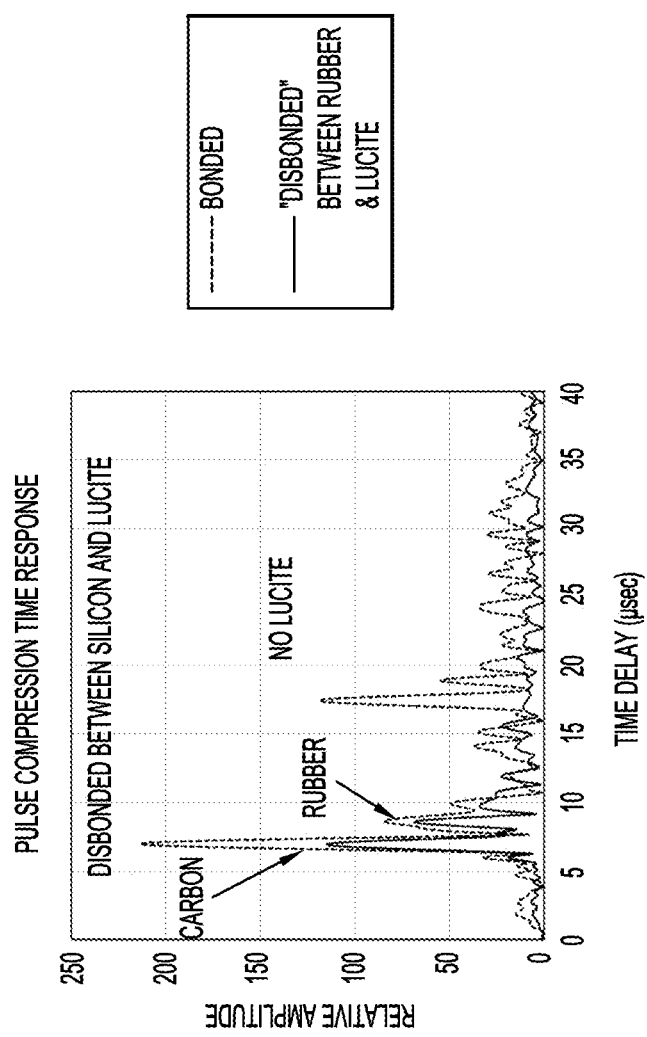
FIG. 19C is an example time domain plot of compressed pulses produced by the time domain processor corresponding to the frequency spectrums of FIGS. 19A and 19B, for the case where a first pair of layers of the multilayer test material are disbonded.

FIGS. 19A-19C show inspection results for test material 1702 produced by receiver 104 responsive to the chirp pulse delivered as described in connection with FIG. 17, but in a case where the silicon rubber layer (Layer 2) and the Lucite layer (Layer 3) are disbonded.

With reference to FIG. 19A, there is shown an example first frequency spectrum produced by spectral processor 602. In FIG. 19A, the first frequency spectrum from FIG. 18A (the bonded case) is shown in dotted line for ease of comparison.

With reference to FIG. 19B there is shown an example second frequency spectrum produced by spectral processor 602, as an FFT of the first frequency spectrum from FIG. 19A. The second frequency spectrum prominently shows the resonance frequencies for the carbon phenolic layer (Layer 1), but not the Lucite layer (Layer 3) because of the disbonded layers. In FIG. 19B, the second frequency spectrum from FIG. 18B (the bonded case) is shown in dotted line for ease of comparison.

With reference to FIG. 19C, there is shown an example time domain plot produced by time domain processor 604. The time domain plot includes a compressed pulse (i.e., amplitude peak) corresponding to a reflection from the carbon phenolic layer (Layer 1) and a compressed pulse corresponding to a reflection from the silicon rubber layer (Layer 2), but no compressed pulse corresponding to the Lucite layer (Layer 3) because of the disbonded rubber and Lucite layers.

Figures 20A, 20B:
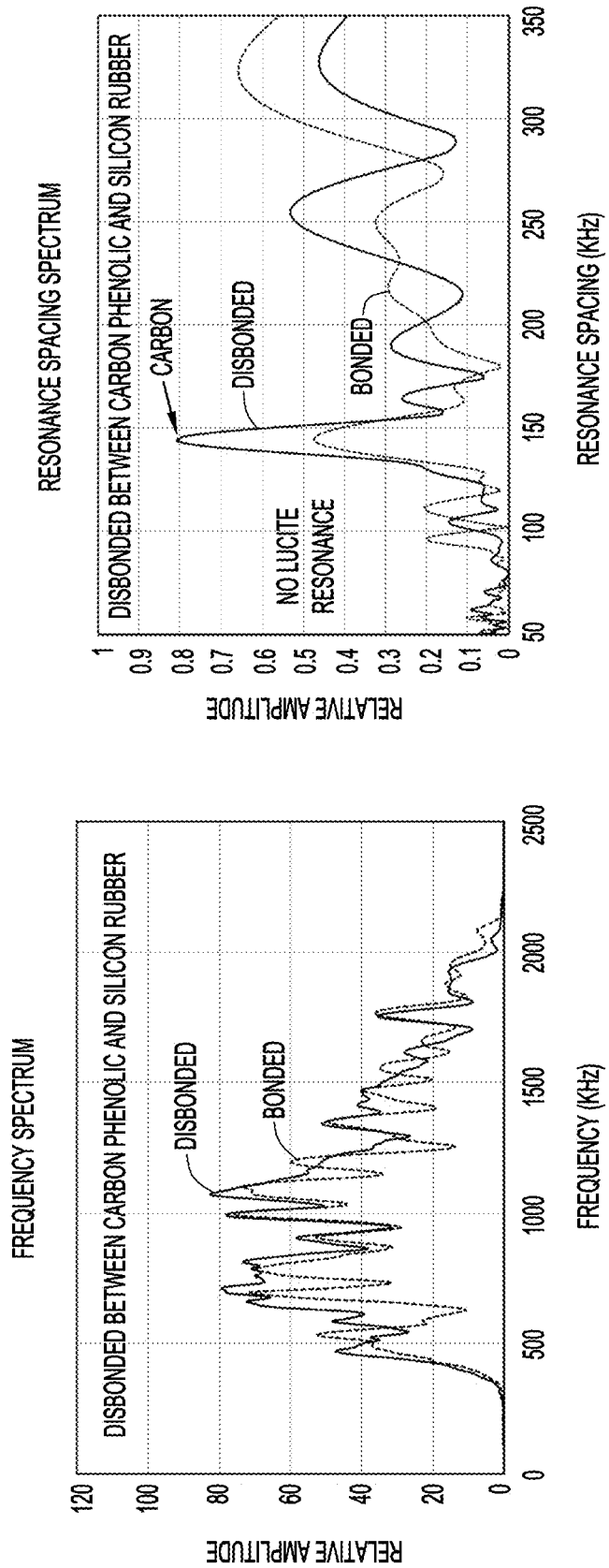
FIG. 20A shows an example first frequency spectrum for the multilayer test material of FIG. 17 in a case where a second pair of the layers of the multilayer test material are disbonded.
FIG. 20B shows an example resonance spacing spectrum for the multilayer test material of FIG. 17, based on the first frequency spectrum of FIG. 20A.

FIGS. 20A-20C show inspection results for test material 1702 produced by receiver 104 responsive to the delivered chirp pulse as described in connection with FIG. 17, but in a case where the carbon phenolic layer (Layer 1) and the silicon rubber layer (Layer 2) are disbonded. In FIG. 20A, the first frequency spectrum from FIG. 18A (the bonded case) is shown in dotted line for ease of comparison.

With reference to FIG. 20A, there is shown an example first frequency spectrum produced by spectral processor 602.

With reference to FIG. 20B there is shown an example second frequency spectrum produced by spectral processor 602, as an FFT of the first frequency spectrum from FIG. 20A. The second frequency spectrum prominently shows the resonance frequencies for the carbon phenolic layer (Layer 1), but not for the Lucite layer (Layer 3) because of the disbonded layers.

With reference to FIG. 20C, there is shown an example time domain plot produced by time domain processor 604. The time domain plot includes a first compressed pulse corresponding to a first chirp pulse reflection from the carbon phenolic layer (Layer 1), a second compressed pulse corresponding to a second chirp pulse reflection from the from the carbon phenolic layer (Layer 1), but no compressed pulse corresponding to either the Lucite layer (Layer 3) or the silicon rubber layer (Layer 2) due to the disbonded layers.

Figure 21:
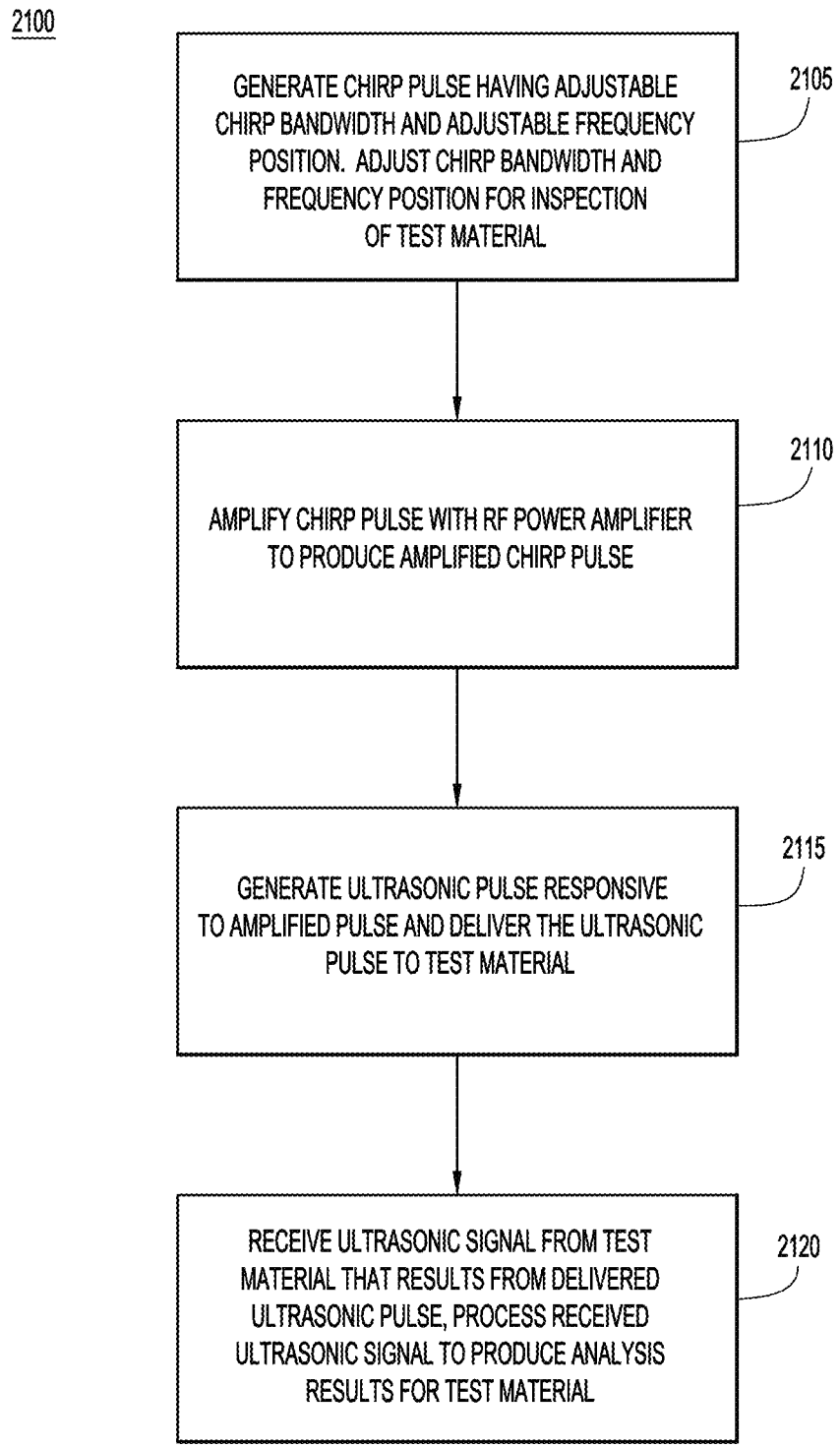
FIG. 21 is a flowchart of an example method performed by the ultrasonic inspection system.

With reference to FIG. 21, there is a flowchart of an example method 2100 performed by ultrasonic inspection system 100. Method 2100 includes various ones of the operations described above.

At 2105, pulse generator 110 generates chirp pulse 112 having a chirp bandwidth. Pulse generator 110 is able to adjust the chirp bandwidth from a lowest chirp bandwidth to a highest chirp bandwidth, and a frequency position of the chirp bandwidth so that the adjusted chirp bandwidth and the frequency position of the chirp bandwidth are suited to inspecting defects or material properties of test material 106.

At 2110, RF power amplifier 120 amplifies chirp pulse 112 to produce amplified chirp pulse 124. RF power amplifier 120 has an operating frequency range greater than the highest chirp bandwidth and a gain that is relatively flat across the highest chirp bandwidth when the frequency position of the highest chirp bandwidth falls anywhere in the operating frequency range.

At 2115, transmit transducer 126 generates an ultrasonic pulse responsive to the amplified pulse and delivers the ultrasonic pulse to test material 106.

At 2120, ultrasonic receiver 104 receives an ultrasonic signal (140/144) from the test material that results from the ultrasonic pulse delivered to the test material, and processes the received ultrasonic signal to produce analysis results 146 indicative of test material defects or properties.

Figure 22:
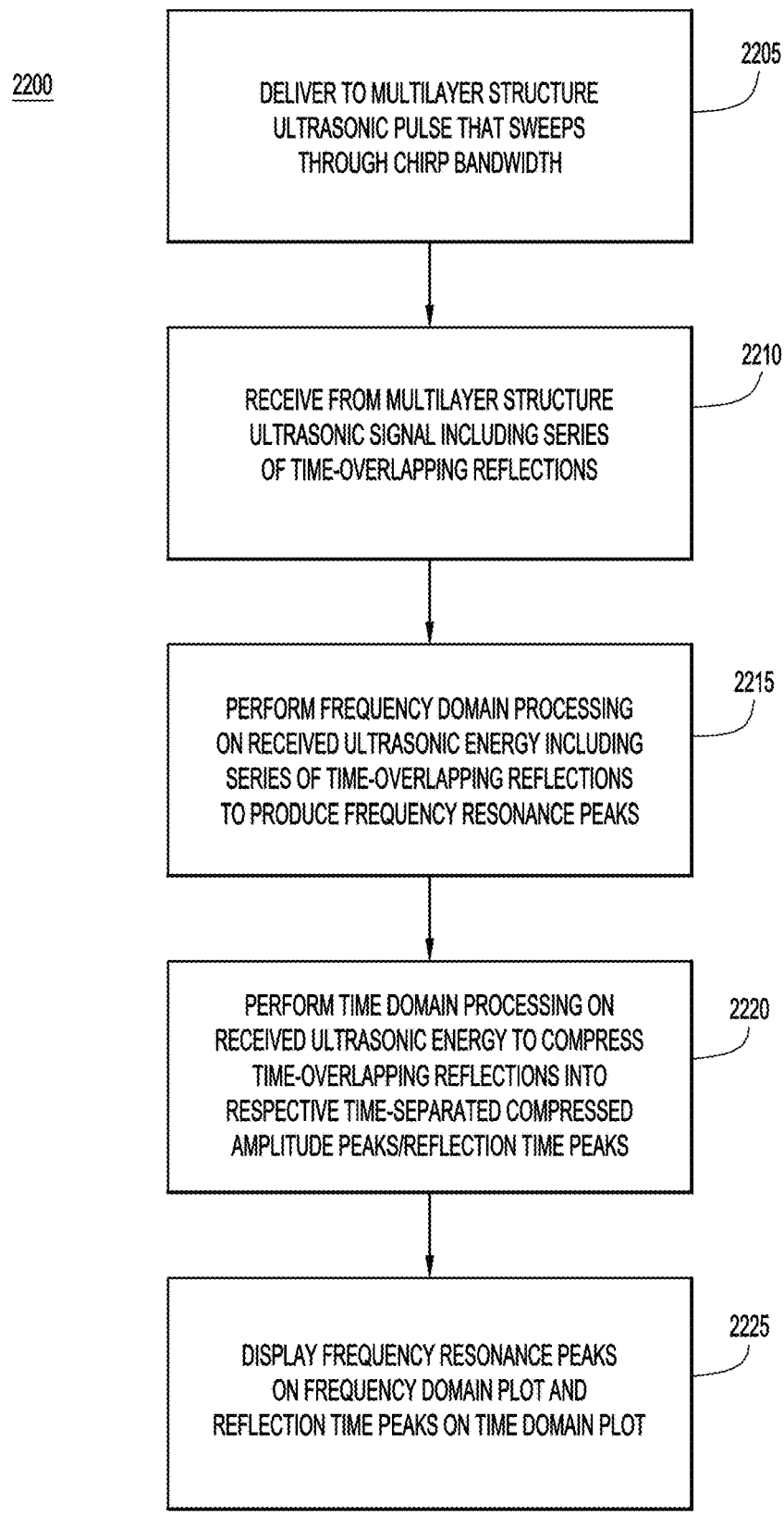
FIG. 22 is a flowchart of another example method performed by the ultrasonic inspection system.

With reference to FIG. 22, there is a flowchart of another example method 2200 performed by ultrasonic inspection system 100. Method 2200 includes various ones of the operations described above.

At 2205, ultrasonic transmitter 102 delivers to a multilayer structure, e.g., test material 106, an ultrasonic pulse that sweeps through a chirp bandwidth.

At 2210, ultrasonic receiver 104 receives from the multilayer structure ultrasonic energy 140/144 including a series of time-overlapping reflections of the pulse delivered to the multilayer structure at 2205 from layers of the multilayer structure. The series of time-overlapping reflections may represent a full multilayer response of test material 106, as described above.

At 2215, spectral processor 602 performs frequency domain processing on the received ultrasonic energy (140/144) including the series of time-overlapping reflections to produce frequency resonance peaks respectively indicative of distinct layers of the multilayer structure.

At 2220, time domain processor 604 performs time domain processing on the received ultrasonic energy (140/144) to compress the series of time-overlapping reflections into respective time-separated compressed amplitude peaks/reflection time peaks. In an embodiment, spectral processor 602 and time domain processor 604 concurrently perform their respective processing on the (same) ultrasonic energy (140/144) including the series of time-overlapping reflections, so as to generate their respective processing results concurrently.

At 2225, output device 138, e.g., a computer display, displays the frequency resonance peaks on a frequency domain plot and displays the reflection time peaks on a time domain plot. The frequency and time domain plots may be displayed concurrently on one or more computer displays.

Figure 23:
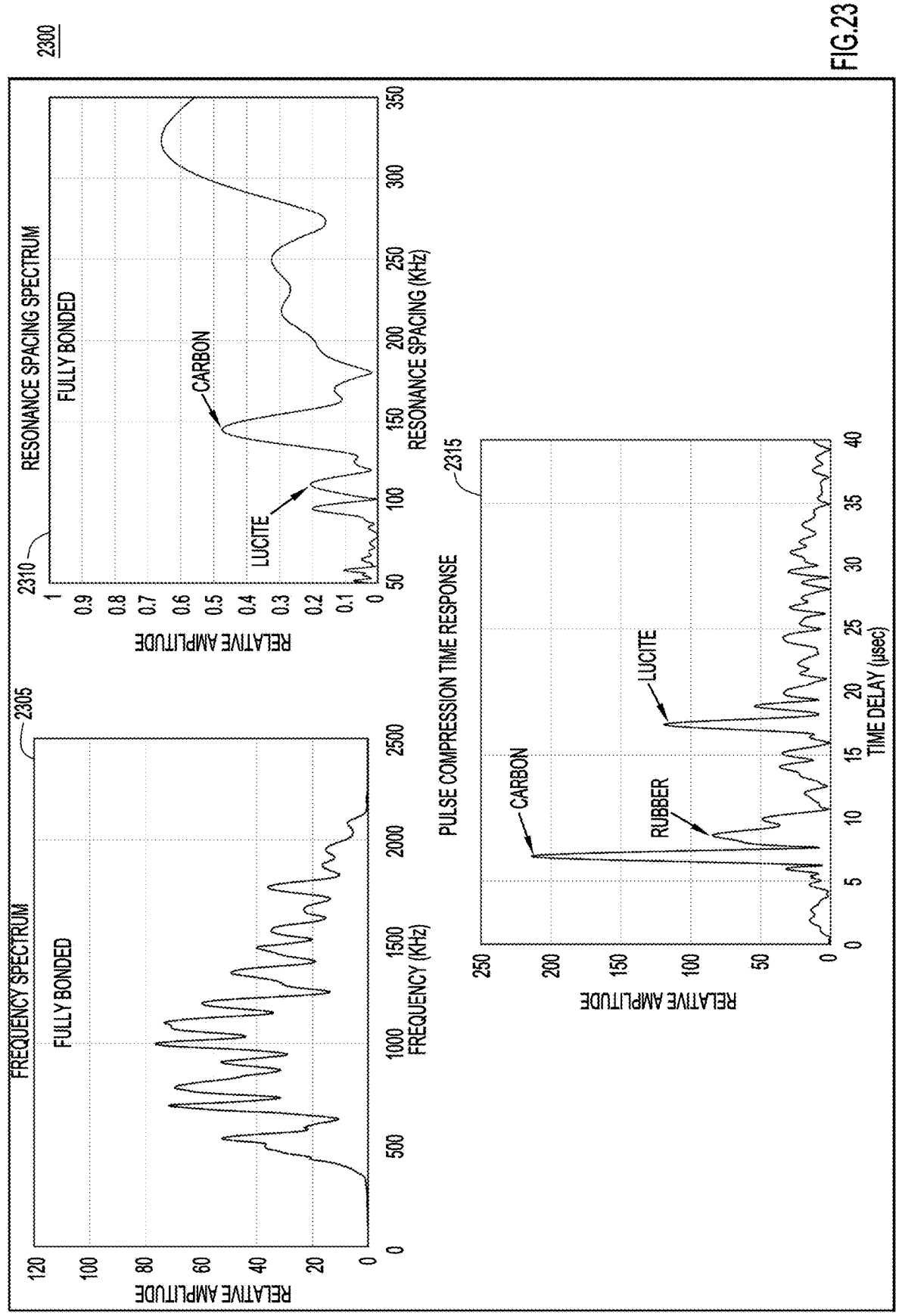
FIG. 23 is an illustration of an example computer display on which plots of a frequency spectrum, a resonance spacing spectrum, and a pulse compression time response are concurrently displayed.

With reference to FIG. 23, there is an illustration of a computer display 2300 (e.g., output device 138) on which plots of a frequency spectrum 2305, a resonance spacing spectrum 2310, and a pulse compression time response 2315 generated by signal processor 136 as described above are concurrently displayed.

Figure 24:
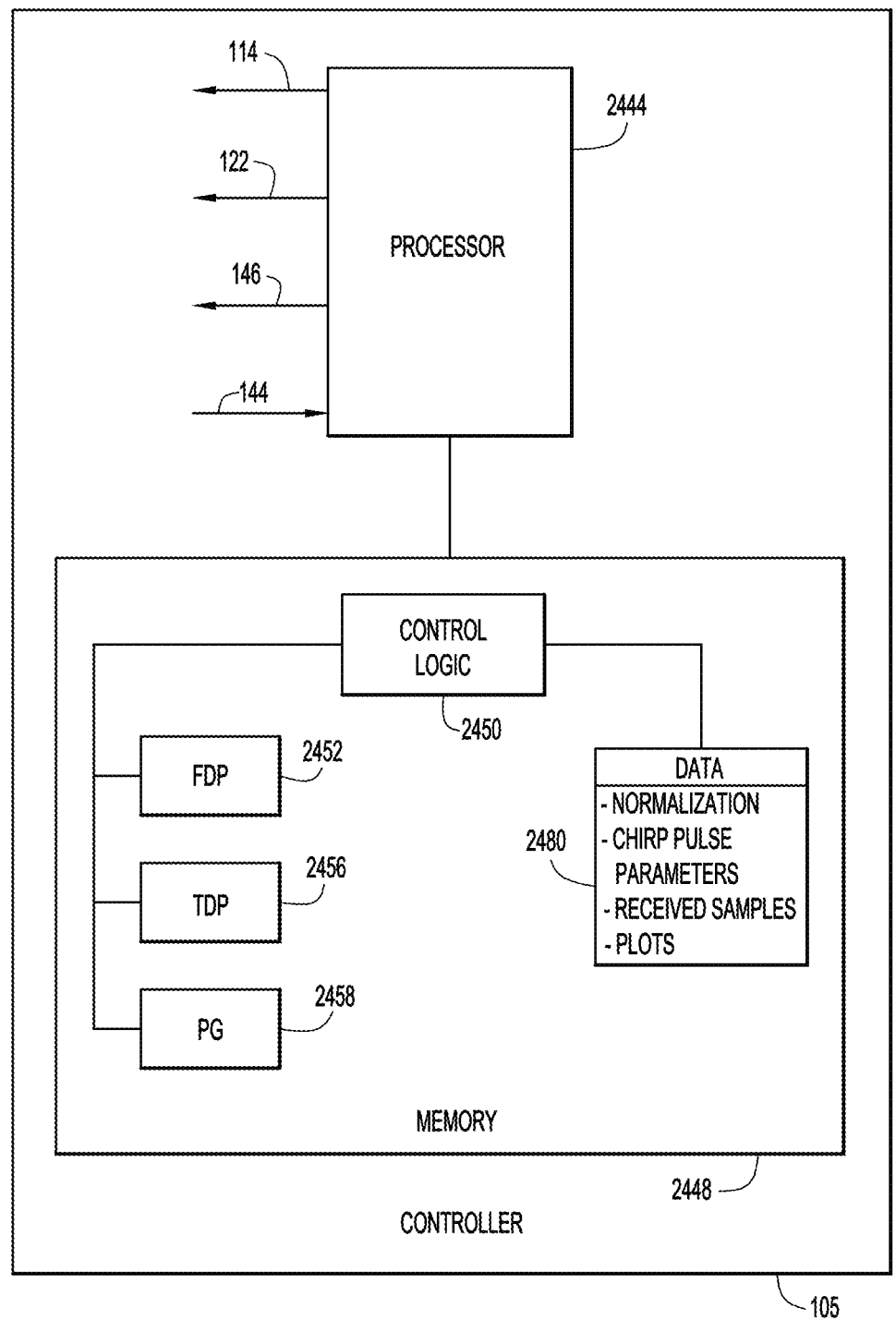
FIG. 24 is a block diagram of an example controller of the ultrasound inspection system.

Reference is now made to FIG. 24, which shows an example block diagram of controller 105 of ultrasound inspection system 100, according to an embodiment. Controller 105 may provide overall control of inspection system, and may also incorporate components of transmitter 102 and ultrasonic receiver 104 described above. There are numerous possible configurations for controller 105 and FIG. 24 is meant to be an example. Controller 105 includes a processor 2444 and memory 2448.

Processor 2444 may include a collection of microcontrollers and/or microprocessors, for example, each configured to execute respective software instructions stored in the memory 2448. Processor 2444 may generate pulse generator control commands 114, gain control signal 122, and analysis results 146. Processor 2444 may also receive digitized received ultrasonic signal 144 from ADC 134. Portions of memory 2448 (and the instruction therein) may be integrated with processor 2444.

The memory 2448 may comprise read only memory (ROM), random access memory (RAM), magnetic disk storage media devices, optical storage media devices, flash memory devices, electrical, optical, or other physical/tangible (e.g., non-transitory) memory storage devices. Thus, in general, the memory 2448 may comprise one or more computer readable storage media (e.g., a memory device) encoded with software comprising computer executable instructions and when the software is executed (by the processor 2444) it is operable to perform the operations described herein. For example, the memory 2448 stores or is encoded with instructions for Control logic 2450 to perform overall control of ultrasonic inspection system 100 and operations described herein related to pulse generator 110 and signal analyzer 136. For example, Control logic 2450 may include frequency domain processor (FDP) logic 2452 to implement the functions of the FDP, time domain processor (TDP) logic 2456 to implement the functions of the TDP, and pulse generator (PG) logic 2458 to implement functions of the pulse generator described above.

In addition, memory 2448 stores data 2480 used and generated by logic 2450-2458, including, but not limited to: normalization information used to normalize the amplitude of the chirp pulse delivered by transmit transducer 126, chirp pulse parameters (e.g., chirp bandwidth, amplitude, frequency position, and frequency sweep characteristic) used by pulse generator 110, samples of digitized ultrasonic receive signal 144 from ADC 134, and analysis results.

Ultrasonic inspection system 100 may be use in many different applications to inspect multiple layer materials and perform bondline analysis, corrosion/defect detection, and other material characterization. Applications include metal/composite bondlines, e.g., helicopter blade bondline inspection; composite/honeycomb bondlines: e.g., helicopter blade—general blade bondline inspection; aging aircraft; aircraft production quality control; corrosion detection; porosity or internal defect analysis.

In summary, in one form, a method is provided.

In summary, in another form, an apparatus is provided.

In summary, in yet another form, a non-transitory processor readable medium is provided. The processor readable medium stores instructions that, when executed by a processor, cause the processor to perform the methods described herein.

The above description is intended by way of example only. Various modifications and structural changes may be made therein without departing from the scope of the concepts described herein and within the scope and range of equivalents of the claims.

What is claimed is:

1. A method comprising:
   delivering to a structure under inspection an ultrasonic chirp pulse having a swept frequency that sweeps through a chirp bandwidth;

receiving from the structure under inspection ultrasonic energy including a series of time-overlapping chirp pulse reflections of the ultrasonic chirp pulse delivered to the structure under inspection from structural features of the structure under inspection;

performing frequency domain processing on the ultrasonic energy including the series of time-overlapping chirp pulse reflections, by performing a first Fourier transform on the ultrasonic energy to produce a first frequency spectrum, and performing a second Fourier transform on the first frequency spectrum to produce a second frequency spectrum that includes frequency resonance peaks respectively indicative of distinct features of the structure under inspection;

performing time domain processing on the ultrasonic energy including the series of time-overlapping chirp pulse reflections, the time domain processing including pulse compression to compress the time-overlapping chirp pulse reflections into respective time-separated reflection time peaks that are not time-overlapping;

displaying the frequency resonance peaks on a frequency domain plot; and displaying the reflection time peaks on a time domain plot.

2. The method of claim 1, wherein the performing the time domain processing includes filtering the series of time-overlapping chirp pulse reflections using a filter response matched to the swept frequency of the ultrasonic chirp pulse delivered to the structure under inspection.

3. The method of claim 1, wherein the swept frequency increases with time.

4. The method of claim 1, wherein the swept frequency decreases with time.

5. The method of claim 1, wherein the performing the frequency domain processing on the ultrasonic energy causes respective frequency resonance peaks corresponding to distinct features of the structure under inspection having a same frequency resonance to overlap in a combined frequency resonance peak such that the distinct features are not separately indicated on the frequency domain plot, but the time domain processing results in the time-separated reflection time peaks that separately indicate the distinct features on the time domain plot.

6. The method of claim 1, further comprising concurrently displaying on one or more displays the frequency resonance peaks on the frequency domain plot and the reflection time peaks on the time domain plot.

7. The method of claim 1, further comprising:
generating a pulse having a swept frequency that sweeps through the chirp bandwidth; and
wherein the delivering includes delivering the ultrasonic chirp pulse to the structure under inspection via an ultrasonic transducer in response to the generated pulse.

8. An apparatus comprising:
an ultrasonic transmitter to deliver to a structure under inspection an ultrasonic chirp pulse having a swept frequency that sweeps through a chirp bandwidth;
an ultrasonic receive transducer to receive from the structure under inspection ultrasonic energy including a series of time-overlapping chirp pulse reflections of the ultrasonic chirp pulse delivered to the structure under inspection from structural features of the structure under inspection;
a frequency domain analyzer to perform frequency domain processing on the ultrasonic energy including the series of time-overlapping chirp pulse reflections, by performing a first Fourier transform on the ultrasonic energy to produce a first frequency spectrum, and performing a second Fourier transform on the first frequency spectrum to produce frequency resonance peaks respectively indicative of distinct features of the structure under inspection;

a time domain analyzer to perform time domain processing on the ultrasonic energy including the series of time-overlapping chirp pulse reflections, the time domain processing including pulse compression to compress the time-overlapping chirp pulse reflections into respective time-separated reflection time peaks that are not time-overlapping; and one or more displays to display the frequency resonance peaks on a frequency domain plot, and the reflection time peaks on a time domain plot.

9. The apparatus of claim 8, wherein the time domain analyzer is configured to perform the time domain processing by filtering the series of time-overlapping chirp pulse reflections using a filter response matched to the swept frequency of the ultrasonic chirp pulse delivered to the structure under inspection.

10. The apparatus of claim 8, wherein the swept frequency increases with time.

11. The apparatus of claim 8, wherein the swept frequency decreases with time.

12. The apparatus of claim 8, wherein the frequency domain analyzer is configured to perform the frequency domain processing on the ultrasonic energy to cause respective frequency resonance peaks corresponding to distinct features of the structure under inspection having a same frequency resonance to overlap in a combined frequency resonance peak such that the distinct features are not separately indicated on the frequency domain plot, but the time domain processing results in the time-separated reflection time peaks that separately indicate the distinct features on the time domain plot.

13. The apparatus of claim 8, wherein the one or more displays concurrently display the frequency resonance peaks on the frequency domain plot and the reflection time peaks on the time domain plot.

14. The apparatus of claim 8, wherein the ultrasonic transmitter is configured to generate a pulse having a swept frequency that sweeps through the chirp bandwidth, the apparatus further comprising an ultrasonic transducer to deliver the ultrasonic chirp pulse to the structure under inspection in response to the generated pulse.

15. A non-transitory computer readable medium storing instructions that, when executed by a processor of an ultrasonic inspection system configured to including an ultrasonic transmitter and an ultrasonic receive system, cause the processor to:
cause delivery of an ultrasonic chirp pulse having a swept frequency that sweeps through a chirp bandwidth to a structure under inspection;
receive from the structure under inspection ultrasonic energy including a series of time-overlapping chirp pulse reflections of the ultrasonic chirp pulse delivered to the structure under inspection from structural features of the structure under inspection;
perform frequency domain processing on the ultrasonic energy including the series of time-overlapping chirp pulse reflections, by performing a first Fourier transform on the ultrasonic energy to produce a first frequency spectrum, and performing a second Fourier transform on the first frequency spectrum to produce frequency resonance peaks respectively indicative of distinct features of the structure under inspection;

perform time domain processing on the ultrasonic energy including the series of time-overlapping chirp pulse reflections, the time domain processing including pulse compression to compress the time-overlapping chirp pulse reflections into respective time-separated reflection time peaks that are not time-overlapping;

generate for display the frequency resonance peaks on a frequency domain plot; and generate for display the reflection time peaks on a time domain plot.

16. The non-transitory computer readable medium of claim 15, wherein the instructions that cause the processor to perform the time domain processing include instructions that cause the processor to filter the series of time-overlapping chirp pulse reflections using a filter response matched to the swept frequency of the ultrasonic chirp pulse delivered to the structure under inspection.

17. The non-transitory computer readable medium of claim 15, wherein the swept frequency increases with time.

18. The non-transitory computer readable medium of claim 15, wherein the swept frequency decreases with time.

19. The non-transitory computer readable medium of claim 15, wherein the instructions that cause the processor to perform frequency domain processing on the ultrasonic energy cause respective frequency resonance peaks corresponding to distinct features of the structure under inspection having a same frequency resonance to overlap in a combined frequency resonance peak such that the distinct features are not separately indicated on the frequency domain plot, but the time domain processing results in the time-separated reflection time peaks that separately indicate the distinct features on the time domain plot.

20. The non-transitory computer readable medium of claim 15, wherein the instructions that cause the processor to generate for display the frequency resonance peaks and the reflection time peaks include instructions that cause the processor to generate for concurrent display the frequency resonance peaks on the frequency domain plot and the reflection time peaks on the time domain plot.

* * * * *